(12) United States Patent
Yun

(10) Patent No.: US 8,298,790 B2
(45) Date of Patent: Oct. 30, 2012

(54) METHODS FOR EFFECTIVELY COEXPRESSING IL-12 AND IL-23

(75) Inventor: Chae-Ok Yun, Seoul (KR)

(73) Assignee: Chae-Ok Yun, Seoul (KR)

( * ) Notice: Subject to any disclaimer, the term of this patent is extended or adjusted under 35 U.S.C. 154(b) by 804 days.

(21) Appl. No.: 12/373,546

(22) PCT Filed: Jan. 17, 2008

(86) PCT No.: PCT/KR2008/000301
§ 371 (c)(1),
(2), (4) Date: Jan. 13, 2009

(87) PCT Pub. No.: WO2008/140173
PCT Pub. Date: Nov. 20, 2008

(65) Prior Publication Data
US 2011/0124048 A1    May 26, 2011

(30) Foreign Application Priority Data
May 14, 2007  (KR) .................. 10-2007-0046591

(51) Int. Cl.
*C12P 21/04* (2006.01)
*C12N 15/00* (2006.01)
*C12N 5/00* (2006.01)

(52) U.S. Cl. .................. 435/69.52; 435/70.1; 435/70.3; 435/455; 435/456; 435/476; 435/320.1; 435/325

(58) Field of Classification Search ........................ None
See application file for complete search history.

(56) References Cited

OTHER PUBLICATIONS

Lee et al. Enhanced Antitumor Effect of Oncolytic Adenovirus Expressing Interleukin-12 and B7-1 in an Immunocompetent Murine Model Clin. Cancer Res., 2006, vol. 12, pp. 5859-5868.*
Happell et al.Pulmonary Interleukin-23 Gene Delivery Increases Local T-Cell Immunity and Controls Growth of Mycobacterium tuberculosis in the Lungs. Infection and Immunity, 2005, vol. 73, pp. 5782-5788.*
Watford et al. The biology of IL-12: coordinating innate and adaptive immune responsesCytokine & Growth Factor Reviews. 2003, vol. 14, pp. 361-368.*
Tahara, H. et al., "Effective eradication of established murine tumor with IL-12 gene therapy using a polycistronic retroviral vector," J. of Immunology, vol. 154(12), pp. 6466-6474 , Jun. 15, 1995.
Shimozato, O., et al., "The secreted form of the p40 subunit of interleukin (IL)-12 inhibits IL-23 functions and abrogates IL-23-mediated antitumor effects," Immunology, vol. 117(1), pp. 22-28, Jan. 2006.
McMonagle, E.L., et al., "Production of biological active equine interleukin 12 through expression of p35, p40, and single chain IL-12 in mammalian and baculovirus expression system," Equine Veterinary Journal. vol., 33(7), pp. 693-698 (Nov. 2001) (Only Abstract is attached).
Wang, X.H., et al., "In vitro gene therapy of hepatocellular carcinoma using replication-defective and tumor-specific replication-competent adenovirus carrying interleukin-12 gene," Chinese J. of Oncology (Zhonghua Zhong Liu Za Zhi), vol. 26 (10), pp. 581-584 (Oct. 2004) (Only Abstract is attached).
Kaiga, T., et al., "Systemic administration of IL-23 induces potent antitumor immunity primarily mediated through Th1-type response in association with the endogenously expressed Il-12," J. of Immunology, vol. 178(12), pp. 7571-7580 (Jun. 15, 2007).
Shan, B.E. et al., "Antitumor activity and immune enhancement of murine interleukin-23 expressed in murine color carcinoma cells," Cellular and Molecular Immunology, vol. 3(1), pp. 47-52 (Feb. 2006).

* cited by examiner

*Primary Examiner* — Deborah Crouch
(74) *Attorney, Agent, or Firm* — Sughrue Mion, PLLC

(57) ABSTRACT

Disclosed is a method for coexpressing IL-12 (interleukin-12) and IL-23 (interleukin-23), which comprises the steps of: (a) preparing vectors comprising monocistronic expression constructs of each of nucleotide sequences encoding the p35 subunit, the p40 subunit and the p19 subunit, or preparing a vector comprising a polycistronic expression construct of nucleotide sequences encoding the p35 subunit, the p40 subunit and the p19 subunit; (b) transforming the expression constructs into a host cell; and (c) culturing the transformed host cell to obtain IL-12 and IL-23, a vector for coexpressing IL-12 and IL-23, and a pharmaceutical anti-tumor composition comprising the vectors.

15 Claims, 10 Drawing Sheets
(2 of 10 Drawing Sheet(s) Filed in Color)

The symbol "★" denotes mutated Rb (retinoblastoma) binding sites in E1A regions in which a glutamic acid residue (Glu) positioned at amino acid 45 in CR1 is replaced by glycine (Gly) and 7 amino acid residues (DLTCHEA) in CR2 are replaced by 7 glycine residues (GGGGGGG).

Fig..2a
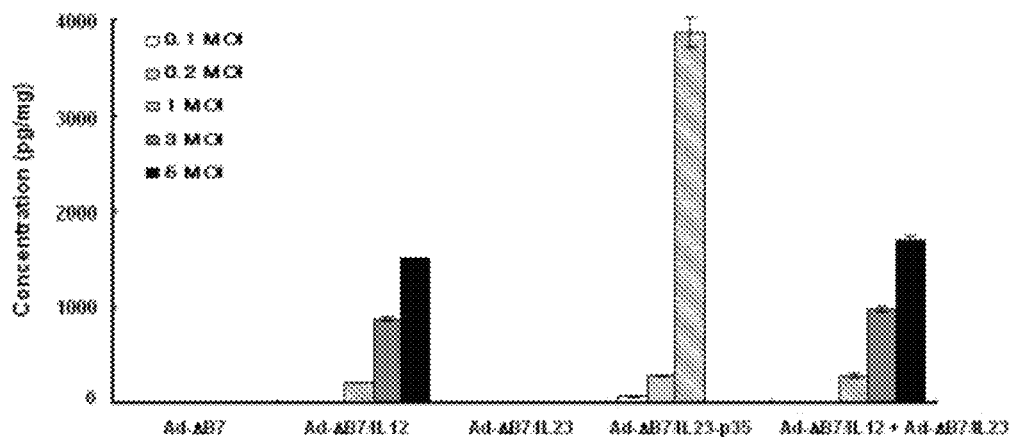
Fig. 2b
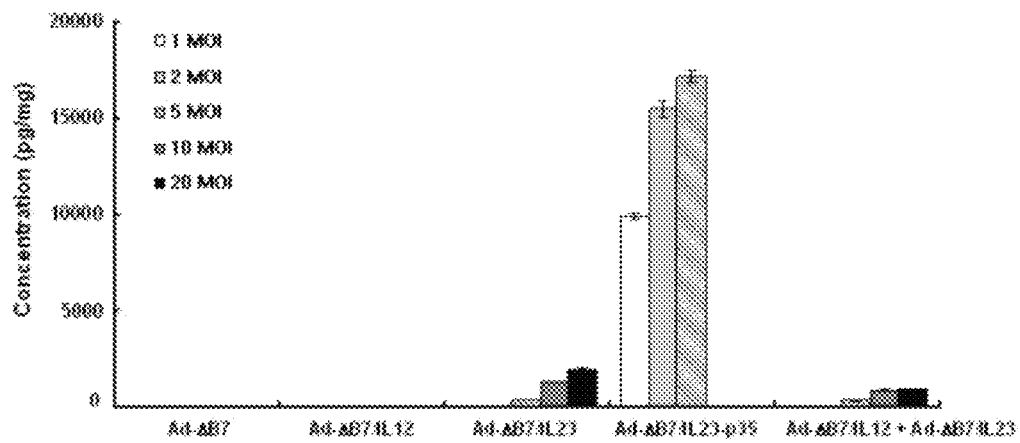

(A) p40 Western blot

(B) p19 Western blot (A) p40 Western blot (B) p19 Western blot

A. Anti-tumor effect

B. Survival rate

METHODS FOR EFFECTIVELY COEXPRESSING IL-12 AND IL-23

This is a National Stage application under 35 U.S.C. §371 of PCT/KR2008/000301 filed on Jan. 17, 2008, which claims priority from Korean patent application 10-2007-0046591 filed on May 14, 2007, all of which are incorporated herein by reference.

BACKGROUND OF THE INVENTION

1. Field of the Invention

The present invention relates to a method and a recombinant vector for coexpressing IL-12 (interleukin-12) and IL-23 (interleukin-23), and a pharmaceutical anti-tumor composition.

2. Background of Technique

Cancer is a disease in which human normal cells escape a cell-cycle control due to genetic mutations caused by various carcinogens and exhibit immortal proliferation, resulting in infiltration into surrounding tissue and metastasis into other internal organs or tissues through blood and lymphatic vessels. Because most cancers were diagnosed after the occurrence of metastasis into other organs or tissues without apparent symptoms, surgical operations, radiotherapy and anti-tumor chemotherapy in use as current therapies have exhibited many limitations. Therefore, novel approaches for effective therapy different from current therapies have been now needed urgently. In this connection, gene therapy and immunotherapy have been actively researched as novel therapeutic methods for various types of cancer diseases[1-3].

Immunotherapy of cancer is aimed to specifically remove cancer cells by boosting the innate immune system. In the early 20th century, Paul and his colleagues[4] asserted that human innate immune system could recognize and remove tumors, suggesting the possibility of anti-tumor immunotherapy for the first time and in the middle 20th century, Gross and his colleagues[5] first demonstrated Paul's hypothesis using animal models.

Thereafter, the theory underlying immune surveillance was founded by Burnet and Thomas[6-8]. Due to the rapid development of genetic engineering and molecular immunology, immune cells and their action mechanisms inducing anti-tumor immune response were revealed, resulting in new turning point in the field of anti-tumor immunotherapy. Much interests and researches have been progressed up to date.

In spite of the rapid development and many efforts, immunotherapy has revealed many limitations to treat cancers. Because cancer cells could avoid ingeniously the immune system through various strategies and escape from activated anti-tumor immune response, they could proliferate continuously in the event. To be free from these limitations, the immune response against tumors has been induced by introducing immunostimulatory cytokine genes directly into cancer cells for producing and secreting cytokines in cancer cells per se, such that cancer cells are specifically removed.

The genes encoding immunostimulatory molecules with anti-tumoric effects include IL-2[9-10] (interleukin-2), IL-4[11-12], IL-7[13], IL-12[14], G-CSF (granulocyte colony-stimulating factor)[15], GM-CSF (granulocyte macrophage colony-stimulating factor)[16] and IFN-γ[17] (interferon-γ). Of them, IL-12 is a heterodimeric protein consisting of p35 and p40 and is secreted from antigen-presenting cells (APC) such as monocytes, macrophages, and dendritic cell. In addition, it activates cancer-killing cytotoxic T-lymphocyte (CTL) and natural killer (NK) cells to induce secretion of IFN-γ and elevation of their oncolytic activity. It has been also known that IL-12 stimulated naive CD4+ lymphocytes to differentiate into T-helper 1 (Th1) cells, resulting in induction and enhancement of cell-mediated immune responses responsible for anti-tumor activities, and inhibited cancer metastasis. On the basis of the findings described above, our laboratory has reported anti-tumor effects of IL-12 using YKL-1 (Ad-ΔE1B55) as the oncolytic adenovirus with the deleted E1B 55 kDa gene.

IL-23 having a similar structure with IL-12 is composed of p40 and p19 as a member of IL-12 superfamily, and is secreted from antigen-presenting cells (APC) such as monocytes[18], macrophages[19] and dendritic cell[20]. It has been known that IL-23 activated APC and induced not only the secretion of IFN-γ and IL-12[20] but also the proliferation of memory T-cells and the secretion of IFN-γ[20]. Especially, IFN-γ induced by IL-12 and IL-23 promotes the expression of major histocompatibility complex (MHC) in APC and increases the antigen-presenting ability. In this regard, IL-23 not only induces the activation of CTL and helper T-lymphocytes through giving immunogenicity to cancer cell, but also increases the oncolytic activity of NK cells. Given the reports up to date, it is expected that anti-tumor effects would be enhanced where both IL-12 and IL-23 having similarities with each other in terms of structure and function act simultaneously. That is, the activation action of a pair of IL-12 and IL-23 on APC becomes more prominent than alone action of either IL-12 or IL-23, and in turn the pairing action induce the secretion of not only IL-12 and IL-23 but also IFN-γ more strongly, contributing to greater influence on all molecular events underlying anti-tumor effect relating to IL-12 and IL-23[21].

For applying effectively adenoviral gene therapy for cancers to practical therapeutics, the development of adenovirus having both the specificity to kill selectively cancer cells without side effects on surrounding normal cells and the capability to kill effectively cancer cells is indispensable. However, because 1st replication-incompetent adenoviruses in which the E1A gene essential for adenovirus replication was deleted, exhibited the infectiveness in only the first generation, they induced anti-tumor activity solely in infected cells and a very small number of surrounding cells, rendering them to have serious problems in clinical applications. To overcome such problems, our laboratory reported both cancer-specific proliferation and oncolytic effects through the development of the E1B 55 kDa-deleted tumor-specific adenovirus, YKL-1 (Ad-ΔE1B55), which could be proliferated selectively in cancer cells lacking functional p53, tumor-inhibitory protein[24]. The oncolytic adenovirus which could proliferate selectively in the cancer cells and kill them, exhibited therapeutic effects in primarily infected cells and in turn proliferated adenoviruses infected and killed surrounding tumor cells. These features lead to dramatic cancer treatment efficacy with little or no adverse effects due to their incompetence of replication in normal cell. However, the proliferation of YKL-1 adenovirus was restricted relatively as compared with wild type (WT) adenovirus, and its cytotoxicity was reduced significantly, resulting in low anti-tumor effects[25].

To augment such lower cell-killing ability of YKL-1 adenovirus, our laboratory had developed and reported in vivo and in vitro excellent anti-tumor effects of Ad-ΔB7 adenovirus showing enhanced cell-killing potential through the deletion of E1B 19 kDa region and significantly improved oncolytic activity through substituting Gly (G) for Glu (E) in 45 position within CR1 region and seven GGGGGGG for seven DLTCHEA in CR2 region. That is, the Ad-ΔB7 adenovirus has not only enhanced oncolytic activity against cancer cells due to increased apoptosis-inducing potential by the deletion of the E1B 19 kDa region to inhibit apoptosis, but also improved oncolytic selectivity by the deletion of the Rb-binding region in the E1A gene and substitution with Gly residue to enable it to replicate only in Rb-mutated cancer cells.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to coexpress IL-12 and IL-23 having anti-tumor effect in much higher efficiency and to develop gene therapeutics with enhanced anti-tumor effect. As results, we have discovered a suitable combination of genes encoding the subunits of IL-12 and IL-23 could permit to coexpress efficiently IL-12 and IL-23 and to exhibit enhanced anti-tumor effects.

Accordingly, it is an object of the invention to provide a method for coexpressing IL-12 and IL-23.

It is another object of this invention to provide a recombinant vector for coexpressing IL-12 and IL-23.

It is still another object of this invention to provide a pharmaceutical anti-tumor composition.

Other objects and advantages of the present invention will become apparent from the detailed description to follow taken in conjugation with the appended claims and drawings.

In one aspect of this invention, there is provided a method for coexpressing IL-12 (interleukin-12) and IL-23 (interleukin-23), which comprises the steps of:

(a) preparing vectors comprising monocistronic expression constructs of each of nucleotide sequences encoding the p35 subunit, the p40 subunit and the p19 subunit, or preparing a vector comprising a polycistronic expression construct of nucleotide sequences encoding the p35 subunit, the p40 subunit and the p19 subunit;

(b) transforming the expression constructs into a host cell; and (c) culturing the transformed host cell to obtain IL-12 and IL-23.

In another aspect of this invention, there is provided a recombinant vector for coexpressing IL-12 (interleukin-12) and IL-23 (interleukin-23), which comprises the following expression constructs:

(i) (i-1) the polycistronic expression construct comprising a promoter operable in eukaryotic cells-p19 encoding nucleotide sequence-IRES-p40 encoding nucleotide sequence-polyadenylation sequence, and (i-2) the monocistronic expression construct comprising a promoter operable in eukaryotic cells-p35 encoding nucleotide sequence-polyadenylation sequence; (ii) (ii-1) the polycistronic expression construct comprising a promoter operable in eukaryotic cells-p40 encoding nucleotide sequence-IRES-p19 encoding nucleotide sequence-polyadenylation sequence, and (ii-2) the monocistronic expression construct comprising a promoter operable in eukaryotic cells-p35 encoding nucleotide sequence-polyadenylation sequence; (iii-1) the polycistronic expression construct comprising a promoter operable in eukaryotic cells-p35 encoding nucleotide sequence-IRES-p40 encoding nucleotide sequence-polyadenylation sequence, and (iii-2) the monocistronic expression construct comprising a promoter operable in eukaryotic cells-p19 encoding nucleotide sequence-polyadenylation sequence; (iv) (ii-1) the polycistronic expression construct comprising a promoter operable in eukaryotic cells-p40 encoding nucleotide sequence-IRES-p35 encoding nucleotide sequence-polyadenylation sequence, and (iv-2) the monocistronic expression construct comprising a promoter operable in eukaryotic cells-p19 encoding nucleotide sequence-polyadenylation sequence; (v) (v-1) the polycistronic expression construct comprising a promoter operable in eukaryotic cells-p19 encoding nucleotide sequence-IRES-p35 encoding nucleotide sequence-polyadenylation sequence, and (v-2) the monocistronic expression construct comprising a promoter operable in eukaryotic cells-p40 encoding nucleotide sequence-polyadenylation sequence; or (vi) (vi-1) the polycistronic expression construct comprising a promoter operable in eukaryotic cells-p35 encoding nucleotide sequence-IRES-p19 encoding nucleotide sequence-polyadenylation sequence, and (vi-2) the monocistronic expression construct comprising a promoter operable in eukaryotic cells-p40 encoding nucleotide sequence-polyadenylation sequence.

The present inventors have made intensive studies to coexpress IL-12 and IL-23 having anti-tumor effect in much higher efficiency and to develop gene therapeutics with enhanced anti-tumor effect. As results, we have discovered a suitable combination of genes encoding the subunits of IL-12 and IL-23 could permit to coexpress efficiently IL-12 and IL-23 and to exhibit enhanced anti-tumor effects.

The principle strategy of the present invention is that IL-12 and IL-23 share the p40 subunit and they may be produced effectively in higher efficiency where p40 homodimer is relatively expressed at lower level than other subunits. For this strategy, the coexpression system for IL-12 and IL-23 has been constructed using p40 subunit-encoding nucleotide sequence as a sharing sequence.

In view of stoichiometry, it might be understood to one of skill in the art that expression systems should be constructed using both subunits of IL-12, i.e., the p35 subunit-encoding nucleotide sequence and the p40 subunit-encoding nucleotide sequence, and both subunits of IL-23, i.e., the p19 subunit-encoding nucleotide sequence and the p40 subunit-encoding nucleotide sequence to effectively coexpress IL-12 and IL-23. Unlikely, the present inventors have discovered that IL-12 and IL-23 could be obtained much effectively at higher yield where one of two p40 subunit-encoding nucleotide sequences was excluded.

The present invention relates to methods and recombinant vectors for coexpressing IL-12 and IL-23. As used herein the term "coexpression" means that nucleotide sequences coding for IL-12 and IL-23 are simultaneously expressed in a single expression system, preferably a single expression vector.

The invention utilizes the p35 subunit-encoding nucleotide sequence, the p40 subunit-encoding nucleotide sequence, and the p19 subunit-encoding nucleotide sequence. The term "p35 subunit", "p40 subunit" and "p19 subunit" is used herein to intend to include their analogues showing their biologically inherent functions as well as those exemplified by the following Examples.

The amino acid sequences of p35, p40 and p19 used in the instant invention are described in GenBank Accession Nos. AAD56385, AAD56386 and AAH67511, respectively (for mouse p35, p40 and p19, see the sequences described in each GenBank Accession Nos. AAA39292, AAA39296 and AAG37231). The nucleotide sequences of p35, p40 and p19 useful in this invention encode the above amino acid sequences, preferably comprising the sequences corresponding to CDS (coding sequence) in sequences described in each GenBank Accession Nos. AF180562, AF180563 and BC067511 (for mouse p35, p40 and p19, see CDS of sequences described in each GenBank Accession Nos. M86672, M86671 and AF301619).

According to the present method, the vector constructs comprising monocistronic expression constructs of each of nucleotide sequences encoding the p35 subunit, the p40 subunit and the p19 subunit are prepared, or alternatively the vector constructs comprising a polycistronic expression construct of nucleotide sequences encoding the p35 subunit, the p40 subunit and the p19 subunit are prepared.

The term "expression construct" as used herein means essential elements for gene expression, containing a nucleotide sequence of interest to express and expression regulatory sequences (e.g. promoter). Preferably, these expression constructs contain a transcription regulatory sequence-nucleotide sequence of interest to express-polyadenylation sequence.

As used herein the term "monocistronic expression construct" means that a gene is expressed in a single expression construct. The term "polycistronic expression construct" means that two or more genes are expressed in a single expression construct.

According to the present method, the vectors may be constructed for expressing each of nucleotide sequences encoding p35, p40 and p19 in a respective expression construct. For example, the vector may be constructed to contain each of three expression constructs, e.g., a promoter-p35 nucleotide sequence-polyadenylation sequence, a promoter-p40 nucleotide sequence-polyadenylation sequence and a promoter-p19 nucleotide sequence-polyadenylation sequence.

The monocistronic expression constructs comprise (i) a promoter operable in eukaryotic cells-p35 subunit encoding nucleotide sequence-polyadenylation sequence, (ii) a promoter operable in eukaryotic cells-p40 subunit encoding nucleotide sequence-polyadenylation sequence, and (iii) a promoter operable in eukaryotic cells-p19 subunit encoding nucleotide sequence-polyadenylation sequence.

The term "a promoter operable in eukaryotic cells" as used herein means a transcription regulatory sequence capable of inducing the transcription of genes of interest in eukaryotic cells. Each of subunit-encoding nucleotide sequences is operatively linked to the promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

In addition, the vectors may be constructed to permit express nucleotide sequences of p35, p40 and p19 in polycistronic expression construct. These polycistronic expression construct may be constructed in various manners, most preferably by positioning IRES (internal ribosomal entry site) between the nucleotide sequences of the subunits.

According to a preferred embodiment, the polycistronic expression construct comprises a promoter operable in eukaryotic cells-nucleotide sequence encoding one of the three subunits-IRES-nucleotide sequence encoding another of the three subunits-polyadenylation sequence-IRES-nucleotide sequence encoding the other of the three subunits-polyadenylation sequence. For example, the tricistronic expression construct such as "promoter-p35 sequence-IRES-p40 sequence-IRES-p19 sequence-polyadenylation sequence" may be constructed. The order of the p35, p40 and p19 sequence is not restricted particularly in the polycistronic expression construct. Also, the two sequences of the subunit sequences may be constructed in a bicistronic form and the other sequence in a monocistronic form.

More preferably, the vector in the step (a) comprises (i) the polycistronic expression construct comprising a promoter operable in eukaryotic cells-(i-1) nucleotide sequence encoding one of the three subunits-IRES-(i-2) nucleotide sequence encoding another of the three subunits-polyadenylation sequence, and (ii) the monocistronic expression construct comprising a promoter operable in eukaryotic cells-(ii-1) nucleotide sequence encoding the other of the three subunits-polyadenylation sequence. For example, the bicistronic expression construct such as "promoter-p19 sequence-IRES-p40 sequence-polyadenylation sequence" and the monocistronic expression construct such as "promoter-p35 sequence-polyadenylation sequence" may be prepared. The order and position of the p35, p40 and p19 sequences is not restricted particularly in the polycistronic expression construct.

According to a preferred embodiment, the expression construct is constructed in a polycistronic manner. Most preferably, the two sequences of subunit sequences are constructed in a bicistronic form and the other sequence is constructed in a monocistronic form.

According to a preferred embodiment, the vector in the step (a) comprises (i) (i-1) the polycistronic expression construct comprising a promoter operable in eukaryotic cells-p19 encoding nucleotide sequence-IRES-p40 encoding nucleotide sequence-polyadenylation sequence, and (i-2) the monocistronic expression construct comprising a promoter operable in eukaryotic cells-p35 encoding nucleotide sequence-polyadenylation sequence; (ii) (ii-1) the polycistronic expression construct comprising a promoter operable in eukaryotic cells-p40 encoding nucleotide sequence-IRES-p19 encoding nucleotide sequence-polyadenylation sequence, and (ii-2) the monocistronic expression construct comprising a promoter operable in eukaryotic cells-p35 encoding nucleotide sequence-polyadenylation sequence; (iii) (iii-1) the polycistronic expression construct comprising a promoter operable in eukaryotic cells-p35 encoding nucleotide sequence-IRES-p40 encoding nucleotide sequence-polyadenylation sequence, and (iii-2) the monocistronic expression construct comprising a promoter operable in eukaryotic cells-p19 encoding nucleotide sequence-polyadenylation sequence; (iv) (iv-1) the polycistronic expression construct comprising a promoter operable in eukaryotic cells-p40 encoding nucleotide sequence-IRES-p35 encoding nucleotide sequence-polyadenylation sequence, and (iv-2) the monocistronic expression construct comprising a promoter operable in eukaryotic cells-p19 encoding nucleotide sequence-polyadenylation sequence; (v) (v-1) the polycistronic expression construct comprising a promoter operable in eukaryotic cells-p19 encoding nucleotide sequence-IRES-p35 encoding nucleotide sequence-polyadenylation sequence, and (v-2) the monocistronic expression construct comprising a promoter operable in eukaryotic cells-p40 encoding nucleotide sequence-polyadenylation sequence; or (vi) (vi-1) the polycistronic expression construct comprising a promoter operable in eukaryotic cells-p35 encoding nucleotide sequence-IRES-p19 encoding nucleotide sequence-polyadenylation sequence, and (vi-2) the monocistronic expression construct comprising a promoter operable in eukaryotic cells-p40 encoding nucleotide sequence-polyadenylation sequence.

According to more preferred embodiment, the vector in the step (a) comprises (i) (i-1) the polycistronic expression construct comprising a promoter operable in eukaryotic cells-p19 encoding nucleotide sequence-IRES-p40 encoding nucleotide sequence-polyadenylation sequence, and (i-2) the monocistronic expression construct comprising a promoter operable in eukaryotic cells-p35 encoding nucleotide sequence-polyadenylation sequence; or (ii) (ii-1) the polycistronic expression construct comprising a promoter operable in eukaryotic cells-p40 encoding nucleotide sequence-IRES-p19 encoding nucleotide sequence-polyadenylation sequence, and (ii-2) the monocistronic expression construct comprising a promoter operable in eukaryotic cells-p35 encoding nucleotide sequence-polyadenylation sequence.

According to the most preferable embodiment, the vector in the step (a) comprises (i) (i-1) the polycistronic expression construct comprising a promoter operable in eukaryotic cells-p19 encoding nucleotide sequence-IRES-p40 encoding nucleotide sequence-polyadenylation sequence, and (i-2) the monocistronic expression construct comprising a promoter operable in eukaryotic cells-p35 encoding nucleotide sequence-polyadenylation sequence.

According to the present invention, the promoter linked to the subunit sequence, without limitation, is operable in, preferably, animal, more preferably, mammalian cells, to control transcription of the subunit sequence, including the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter. Most preferably, the promoter is CMV promoter.

According to the present invention, the polyadenylation sequence linked to the subunit comprises, without limitation, bovine growth hormone terminator (Gimmi, E. R., et al., *Nucleic Acids Res.*, 17:6983-6998 (1989)), SV40-derived polyadenylation sequence (Schek, N., et al., *Mol. Cell. Biol.*, 12:5386-5393 (1992)), HIV-1 polyA (Klasens, B. I. F., et al., *Nucleic Acids Res.*, 26:1870-1876 (1998)), β-globin polyA (Gil, A., et al., *Cell*, 49:399-406 (1987)), or poliomavirus polyA (Batt, D. B. and G. G. Carmichael, *Mol. Cell. Biol.*, 15:4783-4790 (1995)). The exemplary polyadenylation sequence used in this invention is SV40-derived polyadenylation sequence, which is concretely described in SEQ ID No:2.

IRES useful in the polycistronic expression construct means the sequence capable of CAP-independent translation initiation. The IRES useful in this invention includes the regulatory sequences found in some viruses and cellular RNAs (McBrantney et. al., *Current Opinion in Cell Biology*, 5:961 (1993)). For example, IRES sequences found in 5'- or 3'-UTR in mRNAs of picornavirus such as poliomyelitis virus (Pelletier et al., *Mol. Cell. Biol.*, 8:1103-1112 (1988)), EMCV (Encephalomyocarditis virus; Jang et al., *J. Virol.*, 62:2636-2643 (1988)), human rhinovirus, coxsackie virus, echo virus, poliovirus, and FMDV (foot and mouth disease virus); and IRES sequences found in UTR sequences of retroviruses such as murine leukemia virus and reticuloendotheliosis virus are useful in the present invention. Furthermore, celluar mRNAs having IRES sequence were found in, e.g. BIP protein (Macejak and Sarnow, *Nature*, 353:90-94 (1991)), growth factor (Teerink et al., *Biochem. Biophy. Acts.*, 1264:403-408 (1995)), translation initiation factor eIF4G (Gan and Rhoads, *J. Biol. Chem.*, 271:623-626 (1996)), yeast two transcription factor TFIID and HAP4 (Iizuka et al., *Mol. Cell. Biol.*, 14:7322-7330 (1994)), *Drosophila* Antennapedia (Oh, S. K., et al., *Genes Dev.*, 6:1643-1653 (1992)), Ultrabithorax (Ye, X., et al., *Mol. Cell. Biol.*, 17:1714-1721 (1997)), proto-oncogene c-myc (Nanbru, et al., *J. Biol. Chem.*, 272:32061-32066 (1995); Stoneley, M., *Oncogene*, 16:423-428 (1998)), and VEGF (vascular endothelial growth factor) (Stein, I., et al., *Mol. Cell. Biol.*, 18:3112-3119 (1998)), which are useful in this invention. Also, IRES was found in mRNAs encoding gag precursor of VL30-type murine retrotransposon (Berlioz et al., J. Virol., 69:6400-6407 (1995)) and Friend MLV (FMLV) and Moloney MLV (MoMLV) murine leukemia virus, which are useful in this invention. In addition, XIAP IRES (U.S. Pat. No. 6,171,821) may be used in the invention. IRES used in the Examples is described in SEQ ID NO:1.

The vectors of the invention may be provided in a variety of formats, including (i) plasmids and (ii) viral vectors.

The cytokine-encoding nucleotide sequence may be applied to all usual vector, preferably, plasmid, adenovirus (Lockett L J, et al., *Clin. Cancer Res.*, 3:2075-2080 (1997)), adeno-associated virus (AAV, Lashford L S., et al., *Gene Therapy Technologies, Applications and Regulations* Ed. A. Meager, 1999), retrovirus (Gunzburg W H, et al., Retroviral vectors. *Gene Therapy Technologies, Applications and Regulations* Ed. A. Meager, 1999), lentivirus (Wang G. et al., *J. Clin. Invest.* 104(11):R55-62(1999)), herpes simplex virus (Chamber R., et al., *Proc. Natl. Acad. Sci. USA*, 92:1411-1415 (1995)), vaccinia virus (Puhlmann M. et al., *Human Gene Therapy*, 10:649-657 (1999)). Most preferably, the vetor of this invention is constructed by incorporating the cytokine-encoding nucleotide sequence to adenoviruses.

i. Adenovirus

Adenovirus has been usually employed as a gene delivery vector because of its mid-sized genome, ease of manipulation, high titer, wide target-cell range and high infectivity. Both ends of the viral genome contains 100-200 bp ITRs (inverted terminal repeats), which are cis elements necessary for viral DNA replication and packaging. Because it is known that small region of adenovirus genome is necessary to cis element (Tooza, *J. Moelcular Biology of DNA Tumor viruses*, $2^{nd}$ ED. Cold Spring Harbor Laboratory, Cold Spring Harbor, N.Y. (1981)), adenovirus has the ability for the massive delivery of foreign DNA molecule, which is applied to use the special cell lines as 293. In this view, other adenovirus sequences except cytokine gene contain at least ITR sequence in recombinant adenovirus of the invention.

The E1 region (E1A and E1B) of genome encodes proteins responsible for the regulation of transcription of the viral genome and a few cellular genes. The E2 region (E2A and E2B) encodes proteins responsible for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., *Cell*, 31:543-551 (1982); and Riordan, J. R. et al., *Science*, 245:1066-1073 (1989)).

Therefore, it is preferred that the sequence of p19, p40 and p35 in this invention is inserted into either the deleted E1 region (E1A region and/or E1B region, preferably, E1B region) and/or the deleted E3 region.

According to more preferred embodiment, (i) (i-1) the polycistronic expression construct comprising the promoter operable in eukaryotic cells-p19 encoding nucleotide sequence-IRES-p40 encoding nucleotide sequence-polyadenylation sequence is inserted into the E1B-deleted region or the E3-deleted region, and (i-2) the monocistronic expression construct comprising the promoter operable in eukaryotic cells-p35 encoding nucleotide sequence-polyadenylation sequence is inserted into the E1B-deleted region or the E3-deleted region.

Alternatively, (i) (i-1) the polycistronic expression construct comprising a promoter operable in eukaryotic cells-p19 encoding nucleotide sequence-IRES-p40 encoding nucleotide sequence-polyadenylation sequence is inserted into the E1B-deleted region, and (i-2) the monocistronic expression construct comprising a promoter operable in eukaryotic cells-p35 encoding nucleotide sequence-polyadenylation sequence is inserted into the E3-deleted region.

According to a preferred embodiment, the recombinant adenovirus in this invention is the adenovirus, which contains the deletion of E1B gene and is incapable of the binding ability to the Rb resulting from the mutation of nucleotide sequence encoding Rb-binding region in E1A gene sequence (i.e. CR1, CR2, or CR1 and CR2-encoding nucleotide sequence). More preferably, Glu in 45 position within E1A protein was substituted with Gly and 121-127 amino acid sequence were substituted with Gly, and Cys in 124 position was substituted with Gly. The recombinant adenovirus incapable of Rb-binding ability was disclosed in Patent application No. 2004-0032638 of the present inventors (KCCM-10569).

The structures of the illustrated vectors of this invention are described in FIGS. 1d-1g.

The inserted sequences may be also inserted into the deleted-E4 region. The term "deletion" with reference to viral genome sequences encompasses whole deletion and partial deletion as well.

In nature, adenovirus can package approximately 105% of the wild-type genome, providing capacity for about 2 extra kb of DNA (Ghosh-Choudhury et al., *EMBO J.*, 6:1733-1739 (1987)). In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene delivery system of this invention. A great deal of biochemical and genetic information about adenovirus type 5 is known.

The foreign genes delivered by the present adenoviral gene delivery system are episomal, and therefore, have low genotoxicity to host cells. Therefore, gene therapy using the adenoviral gene delivery system of this invention may be considerably safe.

ii. Retrovirus

Retroviruses capable of carrying relatively large exogenous genes have been used as viral gene delivery vectors in the senses that they integrate their genome into a host genome and have broad host spectrum.

In order to construct a retroviral vector, the cytokine gene is inserted into the viral genome in the place of certain viral sequences to produce a replication-defective virus. To produce virions, a packaging cell line containing the gag, pol and env genes but without the LTR (long terminal repeat) and Ψ components is constructed (Mann et al., *Cell*, 33:153-159 (1983)). When a recombinant plasmid containing the cytokine gene, LTR and Ψ is introduced into this cell line, the Ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513 (1988)). The media containing the recombinant retroviruses is then collected, optionally concentrated and used for gene delivery system.

A successful gene transfer using the second-generation retroviral vector has been reported. Kasahara et al. (*Science*, 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

iii. AAV Vector

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368.

Research results for AAV as gene delivery systems are disclosed in LaFace et al, *Viology*, 162:483486 (1988), Zhou et al., *Exp. Hematol.* (*NY*), 21:928-933 (1993), Walsh et al, *J. Clin. Invest.*, 94:1440-1448 (1994) and Flotte et al., *Gene Therapy*, 2:29-37 (1995). Recently, an AAV vector has been approved for Phase I human trials for the treatment of cystic fibrosis.

Typically, a recombinant AAV virus is made by cotransfecting a plasmid containing the gene of interest (i.e., cytokine gene) flanked by the two AAV terminal repeats (McLaughlin et al., *J. Virol.*, 62:1963-1973 (1988); Samulski et al., *J. Virol.*, 63:3822-3828 (1989)) and an expression plasmid containing the wild type AAV coding sequences without the terminal repeats (McCarty et al., *J. Virol.*, 65:2936-2945 (1991)).

iv. Other Viral Vectors

Other viral vectors may be employed as a gene delivery system in the present invention. Vectors derived from viruses such as vaccinia virus (Puhlmann M. et al., *Human Gene Therapy*, 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., Gene, 68:1-10 (1988)), lentivirus (Wang G. et al., *J. Clin. Invest.*, 104(11): R55-62 (1999)) and herpes simplex virus (Chamber R., et al., *Proc. Natl. Acad. Sci. USA*, 92:1411-1415 (1995)) may be used in the present delivery systems for transferring the cytokine gene into cells.

The recombinant vector was prepared as described above, and transformed into approximate host cell. The introduction into host cell of the vectors can be performed through various methods known to those skilled in the art, for example, microinjection (Capecchi, M. R., *Cell*, 22:479 (1980); and Harland and Weintraub, *J. Cell Biol.* 101:1094-1099 (1985)), calcium phosphate co-precipitation (Graham, F. L. et al., *Virology*, 52:456 (1973); and Chen and Okayama, *Mol. Cell. Biol.* 7:2745-2752 (1987)), electroporation (Neumann, E. et al., *EMBO J.*, 1:841 (1982) and Tur-Kaspa et al., *Mol. Cell. Biol.*, 6:716-718 (1986)), liposome-mediated transfection (Wong, T. K. et al., *Gene*, 10:87 (1980) and Nicolau and Sene, *Biochim. Biophys. Acta*, 721:185-190 (1982); and Nicolau et al., *Methods Enzymol.*, 149:157-176 (1987)), DEAE-dextran treatment (Gopal, *Mol. Cell. Biol.*, 5:1188-1190 (1985)), and particle bombardment (Yang et al., *Proc. Natl. Acad. Sci.*, 87:9568-9572 (1990)).

Afterwards, the transformed host cells are cultured to obtain IL-12 and IL-23. The culture of host cells may be performed by various methods known to those skilled in the art (Sambrook, J., et al., *Molecular Cloning. A Laboratory Manual*, 3$^{rd}$ ED. Cold Spring Harbor Press (2001)).

According to the present invention, the expression levels of IL-12 and IL-23 are dramatically increased in a coexpression system using nucleotide sequences encoding p19, p35 and p40 at a stoichiometric ratio of 1:1:1 without using one p40-encoding nucleotide sequence of either IL-12 or IL-23. Such effective expression makes the present vector to exhibit therapeutic efficacies mediated by IL-12 and/or IL-23. For example, the vector of this invention has plausible anti-tumoric effects.

In another aspect of this invention, there is provided a pharmaceutical anti-tumor composition for treating a cancer, which comprises (a) a therapeutically effective amount of the recombinant adenovirus described previously; and (b) a pharmaceutically acceptable carrier.

The pharmaceutical anti-tumor composition of this invention comprises the vector as an active ingredient and the common descriptions between them are omitted in order to avoid undue redundancy leading to the complexity of this specification.

The vector as an active ingredient in the pharmaceutical composition is the vector of the present invention described hereinabove and therefore the above descriptions can be adapted to the recombinant adenovirus of the pharmaceutical composition. Accordingly, the common descriptions between them are omitted in order to avoid undue redundancy leading to the complexity of this specification.

To effectively elicit anti-tumor effect by recombinant adenoviruses, it is necessary that viruses proliferate and spread to neighboring cells faster than the growth rate of cancer cells to induce oncolytic effect. In addition, a successful cancer-gene therapy using adenoviruses requires enhanced safety as well as high therapeutic benefit. The recombinant adenovirus of this invention increases both viral spreading and apoptosis to exhibit significantly increased anti-tumor effect. In particular, the recombinant adenovirus of this invention having deleted E1B 55 gene shows excellent tumor-specificity in cytotoxicity. For this reason, the recombinant adenovirus of this invention allows to decrease a dosage for cancer therapy, reducing significantly toxicity to normal cells and undesirable immune reactions in vivo.

Since the recombinant adenovirus of this invention has oncolytic effect to a wide variety of tumor cells as described above, the pharmaceutical composition of this invention is useful in treating tumor-related diseases, including stomach cancer, lung cancer, breast cancer, ovarian cancer, liver cancer, bronchogenic cancer, nasopharyngeal cancer, laryngeal cancer, pancreatic cancer, bladder cancer, colon cancer, uterine cervical cancer, brain cancer, prostaic cancer, bone cancer, skin cancer, thyroid cancer, parathyroid cancer and ureter cancer. The term "treatment" as used herein, refers to (i) prevention of tumorigenesis; (ii) suppression and curing of tumor-related diseases or disorders by eradicating tumor cells; and (iii) alleviation of tumor-related diseases or disorders by eradicating tumor cells. Therefore, the term "therapeutically effective amount" as used herein means an amount sufficient to achieve the pharmaceutical effect described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate and mineral oils. The pharmaceutical composition according to the present invention may further include a lubricant, a humectant, a sweetener, a flavoring agent, an emulsifier, a suspending agent and a preservative.

The pharmaceutical composition according to the present invention may be administered via the routes used commonly in gene therapy and preferably, administered parenterally, i.e., by intravenous, intraperitoneal, intramuscular, subcutaneous, or local administration. For example, the pharmaceutical composition may be administered intraperitoneally to treat ovarian cancer and intravenously to treat liver cancer, directly injected to visible tumor mass to treat breast cancer, directly injected to enema to treat colon cancer and directly injected to a catheter to treat bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition and physicians of ordinary skill in the art can determine an effective amount of the pharmaceutical composition for desired treatment. Generally, the pharmaceutical composition of the present invention comprises $1\times10^5$-$1\times10^{15}$ pfu/ml of a recombinant adenovirus and $1\times10^{10}$ pfu of a recombinant adenovirus is typically injected once every other day over two weeks.

According to the conventional techniques known to those skilled in the art, the pharmaceutical composition comprising the recombinant adenovirus according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition comprising the recombinant adenovirus according to the present invention may be utilized alone or in combination with typical chemotherapy or radiotherapy. Such combination therapy may be more effective in treating cancer. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

The features and advantage of the present invention are summarized as follows:

(i) The present invention allow to coexpress IL-12 and IL-23 in much higher efficiency by preparing nucleotide sequences encoding the subunits consisting of IL-12 and IL-23 in a monocistronic or polycistronic form.

(ii) Cells transformed by the present vectors coexpressing IL-12 and IL-23 exhibit higher expression levels of the IL-12 and IL-23 proteins.

(iii) The present vectors coexpressing IL-12 and IL-23, inter alia, the present adenoviruses coexpressing IL-12 and IL-23 exhibit significantly enhanced anti-tumor effects and excellent gene therapy effects against cancers.

BRIEF DESCRIPTION OF THE DRAWINGS

The file of this patent contains at least one drawing executed in color. Copies of this patent with color drawing(s)

will be provided by the Patent and Trademark Office upon request and payment of the necessary fee.

FIGS. 2a-2b represent ELISA results to determine the levels of IL-12 (2a) and IL-23 (2b) expressed by the Ad-ΔB7/IL23-p35 recombinant adenovirus vector.

EXAMPLES

Materials and Methods

1. Cell Lines and Cell Culture

Cell lines used in this invention were human brain cancer cell line (U343), non-small lung cancer cell line (A549), murine melanoma cell line (B16-F10) and human embryonic kidney cell line (HEK293), including adenoviral E1 region in host genome, which was expressed early after infection of adenovirus. All cell lines with the exception of B16-F10 were purchased from American Type Culture Collection (ATCC; Manassas, Va., USA). B16-F10 was purchased from Korean Cell Line Bank (KCLB). Also, all cell lines with the exception of B16-F10 were cultured in Dulbecco's minimal essential medium (DMEM; Gibco BRL) supplemented with 10% fetal bovine serum (Gibco BRL, Grand Island, N.Y.) and penicillin-streptomycin (Gibco BRL) at 37° C. in 5% $CO_2$ incubator. B16-F10 was cultured in RPMI 1640 (Gibco BRL) supplemented with 5% fetal bovine serum and penicillin-streptomycin at 37° C. in 5% $CO_2$ incubator.

2. Experimental Animals

For in vivo anti-tumor experiments, male C57BL/6 mice (6-8 weeks of age) were purchased from SLC (Japan SLC Inc., JP). All mice were maintained in a cabinet kept at 22±2° C. and 40-60% humidity with a 12-hr light/dark cycle and permitted to access pathogen-free feeds (Central Lab. Animal Inc., Seoul, Korea) ad libitum and water.

3. Construction, Generation and Titration of Adenoviruses Expressing IL-12 and IL-23

To prepare adenovirus expressing IL-12 or IL-23, we first constructed an adenovirus expressing murine IL-12 gene. pcDNA3.1-p35/IRES vector was constructed by subcloning about 800 bp fragment of the IRES gene, excised from pcDNA3.1-IRES vector (Invitrogen, Carlsbad, Calif., USA) using EcoRI, into p35 gene of pcDNA3.1-p35 vector (Cytokine Bank, Chonbuk university) behind cut by EcoRI. IRES used in this experiment was described in SEQ ID NO:1 and about 1,007 bp fragment of p40 gene excised from pDNA3.1-p40 (Cytokine Bank, Chonbuk university) using PmeI and XhoI, was subcloned into IRES of pcDNA3.1-IL12 vector behind by EcoRV, generating pcDNA3.1-IL12 vector. Each sequence of used p40 and p35 gene was described in GenBank Accession Nos. M86671 and M86672.

Figure 1A:
FIGS. 1a-1g illustrate the bare recombinant adenoviruses used in this invention and the IL-12 and/or IL-23 gene-carrying recombinant adenoviruses of this invention. The symbol "★" denotes mutated Rb (retinoblastoma) binding sites in E1A regions in which a glutamic acid residue (Glu) positioned at amino acid 45 in CR1 is replaced by glycine (Gly) and 7 amino acid residues (DLTCHEA) in CR2 are replaced by 7 glycine residues (GGGGGGG). The symbol Δ shows the deletion of indicated sequence. Ψ is the sequence containing package signal sequence. Abbreviation: ITR, inverted terminal repeat; Ad, adenovirus; CMV, cytomegalovirus promoter; IX, IX gene of adenovirus; polA, SV40-derived polyadenylation sequence.
Figure 1B:
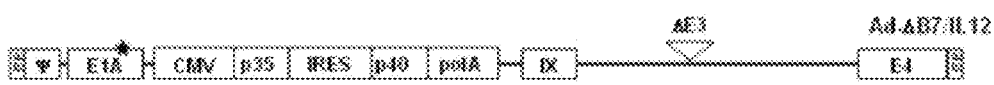

About 2.5 kb fragment of IL-21 (p35/IRES/p40), excised from pcDNA3.1-IL12 vector using SnaBI and SalI, was inserted into pXC1/ΔB7 vector (Kim, J. S., Oncolytic effects of conditionally replicating adenoviruses (CRAds) with mutations in E1A and E1B regions, Yonsei University (2005)), constructing pXC1/ΔB7-IL12 adenovirus E1 shuttle vector. The constructed pXC1/ΔB7-IL12 and vmd1324BstB (Verca, S. B., University of Fribourg, Switzerland; Heider, H., et. al., *Biotechniques*, 28(2):260-265, 268-270 (2000)) was linearized with each NdeI and BstBI digestion. The linearized pXC1/ΔB7-IL12 E1 shuttle vector was then cotransfomed into *E. coli* BJ5183 along with the BstBI-digested vmd1324BstB (Verca, S. B., University of Fribourg, Switzerland) for homologous recombination, generating oncolytic adenovirus Ad-ΔB7-IL12 (FIG. 1(b)).

To prepare adenovirus expressing IL-23, we first isolated macrophage and dendritic cells from the bone marrow of male C57BL/6 mice (6-8 weeks of age) and then p19 gene was synthesized by reverse transcription-polymerase chain reaction (RT-PCR) using primer sets (sense: 5'-ccgctcgagat-gctggattgcagagcagtaat-3', antisense: 5'-ccggaattcttaagctgttg-gcactaagggc-3'). The resulting 590 bp fragments of p19 gene was digested with XhoI and EcoRI, they was inserted into pCA14 vector (Microbix, Ontario, Canada), generating a pCA14-p19. The sequence of used p19 gene was described in GenBank Accession No. AF301619.

Figure 1C:
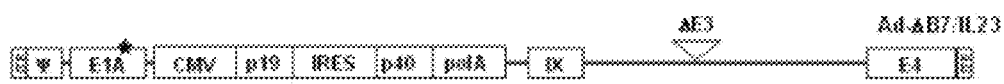

About 800 bp fragment of IRES excised from EcoRI-digested pcDNA3.1-IRES were inserted into p19 of pCA14-p19 vector behind using EcoRI, generating pCA14-p19/IRES vector. Also, p19/IRES derived from pCA14-p19/IRES digested with SnaBI and SalI was inserted into pXC1/ΔB7 vector, generating pXC1/ΔB7-p19/IRES vector. Finally, p40 from pcDNA3.1-p40 digested with HindIII was inserted into pXC1/ΔB7-p19/IRES vector, generating pXC1/ΔB7-IL23 (p19/IRES/p40) adenovirus E1 shuttle vector. The constructed pXC1/ΔB7-IL23 (p19/IRES/p40) shuttle vector was linearized with NruI digestion. The linearized pXC1/ΔB7-IL23 (p19/IRES/p40) shuttle vector was then cotransfomed into *E. coli* BJ5183 along with the BstBI-digested vmd1324BstB (Verca, SB, University of Fribourg, Switzerland) for homologous recombination, generating an oncolytic adenovirus Ad-ΔB7/IL23 (FIG. 1(c)).

Figure 1D:
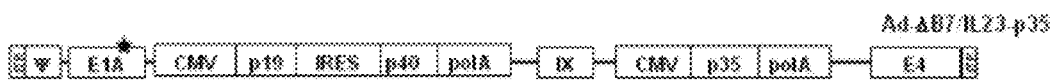
Figure 1E:
Figure 1F:
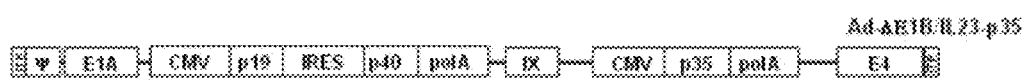
Figure 1G:
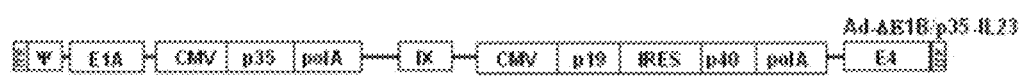

To prepare adenovirus expressing both IL-12 and IL-23, both pSP72ΔE3-p35 E3 shuttle vector and Ad-ΔB7/IL23 total vector were cotransformed into *E. coli* BJ5183, creating adenovirus Ad-ΔB7/IL23-p35 (FIG. 1(d)). The pSP72ΔE3-p35 E3 shuttle vector described above was constructed as follows. About 644 bp fragment of p35 gene, excised from pcDNA3.1-p35 vector (Cytokine Bank, Chonbuk university) using HindIII and EcoRI was subcloned into pSP72 vector (Promega, Madison, Wis.) vector, generating pSP72-p35 vector. p35 gene, excised from pSP72-p35 vector using XhoI and EcoRI, was subcloned into pCA14 vector (Microbix, Ontario, Canada) vector, generating pCA14-p35 vector. The CMV-p35-polA cassette, which could express p35 by CMV promoter, was excised from newly constructed pCA14-p35 vector using BglII and was inserted into BamHI-digested pSP72ΔE3, adenovirus E3 shuttle vector, generating pSP72ΔE3-p35 E3 shuttle vector.

All constructed virus vectors were transformed and produced in HEK293 cells.

4. Analysis of Expression Patterns of IL-12 and IL-23 Proteins

To analyze IL-12 expression by infection with Ad-ΔB7/IL12 or Ad-ΔB7/IL23-p35, ELISA was performed according to the manufacturer's instructions. Human brain cancer cell line U343 and non-small lung cancer cell line A549 were seeded onto 100Φ dish at $1.5\times10^6$ cells per dish and the next day infected with Ad-ΔB7/IL12 or Ad-ΔB7/IL23-p35 at the multiplicity of infections (MOIs) of 1 to 5. At 48 hrs after infection, the media were harvested. The collected cell media or sequentially-diluted IL-12 recombinant proteins each were transferred to 96-well plates coated with a rat anti-IL-12 antibody (Endogen, Woburn, Mass., USA), which recognized specifically IL-12 protein, and incubated at room temperature for 1 hr and washed with phosphate-buffered saline (PBS). A secondary anti-IL-12 antibody conjugated with biotin (Endogen) were added to plates and then incubated at room temperature for 1 hr. After several PBS washing, color was developed for 30 min using streptavidin-conjugated horseradish peroxidase (streptavidin-HRP, Endogen) and the value of absorbance was measured with a microplate reader (Molecular Devices Corp., Sunnyvale, Calif.). The absorbance was measured at each 450 nm and 540 nm and the amounts of IL-12 in the supernatants were quantified by interpolation of a standard curve generated using known amounts of standard recombinant IL-12 (Endogen).

Also, to determine IL-23 expression by infection with Ad-ΔB7/IL23 or Ad-ΔB7/IL23-p35, ELISA was performed. The entire process of ELISA was performed according to the manufacturer's instructions of mouse IL-23 ELISA kit (eBioscience, San Diego, Calif., USA).

IL-12 and IL-23 expression induced by infection with Ad-ΔB7/IL12, Ad-ΔB7/IL23 or Ad-ΔB7/IL23-p35 were also examined using immunoblotting. Human brain cancer cell line U343 was divided into 100Φ dish at $1.5\times10^5$ cells per dish and the next day infected with each Ad-ΔB7/IL12, Ad-ΔB7/IL23 or Ad-ΔB7/IL23-p35 at the MOIs of 1 to 5. At 48 hrs after infection, media were harvested and electrophoresized by sodium dodecyl sulfate-polyacrylamide gel electrophoresis (SDS-PAGE). The gel was electroblotted onto PVDF membrane after SDS-PAGE. Proteins were then detected with primary anti-p40 or anti-p19 antibodies (R & D Systems, Minneapolis, Minn.). After secondary antibodies (Cell Signaling Technology, Beverly, Mass., USA) for primary antibodies were incubated with the membrane, the expression pattern of IL-12 and IL-23 was determined using an ECL according to the manufacturer's instructions (Amersham, Buckinghamshire, UK).

5. Reverse Transcription-Polymerase Chain Reaction (RT-PCR)

The transcription levels of p19, p35 and p40 gene by infection with Ad-ΔB7/IL12, Ad-ΔB7/IL23, Ad-ΔB7/IL23-p35, or Ad-ΔB7/IL23 plus Ad-ΔB7-p35 were examined using RT-PCR. Human brain cancer cell U343 was divided into 6Φ dish at $5\times10^5$ cells per dish and the next day infected with each Ad-ΔB7/IL12, Ad-ΔB7/IL23, Ad-ΔB7/IL23-p35, or Ad-ΔB7/IL23 plus Ad-ΔB7-p35 at MOI of 5. At 48 hrs post-infection, cells were harvested. Total RNA from collected cells was extracted using RNase mini-kit (Qiagen, Valencia, Calif.) and cDNAs were synthesized from total RNA using M-MLV reverse transcriptase. Finally, using p19 primer set (sense: 5'-cctggctgtgcctaggagta-3', antisense: 5'-aggctccctttgaagatg-3'), p35 primer set (sense: 5'-gccagggtcattcagtctc-3', antisense: 5'-ggcacagggtcatcatcaaa-3') and p40 primer set (sense: 5'-agcagttcccctgactctcg-3', antisense: 5'-cagggtactcccagctgacc-3'), the PCR reactions were conducted under the following thermal conditions: 10 min at 94° C. followed by 28 cycles of 30 sec at 94° C., 30 sec at 55° C. and 30 sec at 72° C. and additional 10 min at 72° C. After the PCR reaction was performed, the amount of each mRNA was compared and determined.

6. Examination of Anti-Tumor Effects and Survival Rate Ex Vivo

To examine comparatively ex vivo anti-tumor effects of Ad-ΔB7/IL12, Ad-ΔB7/IL23, and Ad-ΔB7/IL23-p35, tumors were implanted subcutaneous on the abdomen of male C57BL/6 mice (Charles River Laboratories International, Inc., Wilmington, Mass., USA) at 6-8 weeks of age by injecting B16-F10 murine melanoma cells ($5\times10^5$) in 50 μA Hanks' balanced salt solution (HBSS; Gibco BRL). When tumor size reached at a range of 120 to 150 mm$^3$, growth rate and survival rate of tumors were observed after tumors were injected with adenoviruses ($5\times10^9$ VP (virus particles)) and PBS as a negative control at 3 times per 2 days, respectively. After long and short axis of tumor was measured by virginia calipers, the volume of tumors was calculated as the following formula: the volume of tumors=(short axis mm)$^2\times$long axis mm$\times$0.523.

7. Preparation of Murine Splenocytes ex Vivo

Melanoma formed on the abdomen of male C57BL/6 mice as described in Example 6 "Examination of anti-tumor effects and survival rate ex vivo" were injected with adenovirus. Mouse was broken cervical spine about 3-5 days after last injection of virus, cut in the abdomen, and spleen was extracted aseptically and homogenized using rough side of sterile slide. Homogenized splenocytes were resuspended into RPMI 1640 media containing 10% fetal bovine serum (FBS), and then centrifuged at 2000 rpm for 10 min to remove the supernatants. The pellets was incubated with Ammonium-Chloride-Potassium (ACK) lysis buffer (0.15 M NH$_4$Cl, 1 mM KHCO$_3$, 0.1 mM Na$_2$ EDTA, pH 7.2) for 5 min at 4° C. to remove red blood cells. After centrifugation at 2000 rpm for 10 min, the precipitates were then washed 2 times with RPMI 1640 media supplemented with 10% FBS, diluted with trypan-blue (Gibco BRL), and the number of cell was counted.

8. IFN-γ ELISpot Analysis

ELISpot (enzyme-linked immune spot) analysis was performed to examine the activity of tumor-specific immune cells in mice injected with adenovirus. Spleen cells as described in Example 7 "Preparation of murine splenocytes ex vivo" were diluted at $1.5\times10^6$ (cell/ml) on media, and then incubated with IL-2 (100 U/ml) together with pre-radiated B16-F10 cell line for 5 days at 37° C. in 5% $CO_2$ incubator. Cells were precipitated by centrifugation about 5 days after culturing and then washed twice with RPMI 1640 media supplemented with 10% FBS. Each microtiter plate was coated with anti-IFN-γ antibody (Millipore, Bedford, Mass., USA) for 24 hrs, and next day each $1\times10^4$, $3\times10^4$, $9\times10^4$, $2\times10^5$, and $6\times10^5$ splenocytes were divided into microtiter plates and incubated for 15 hrs. After incubation with anti-IFN-γ antibody conjugated with biotin (Millipore, Bedford, Mass., USA) for 2 hrs, the splenocytes were incubated with streptavidin-alkaline phosphatase conjugate (Pharmingen, San Diego, Calif., USA) for 1 hr. After addition of AEC (3-amino-9-ethylcarbazol, Pharmingen, San Diego, Calif., USA) solution as substrates, the number of cells secreting IFN-γ (red color) was counted under stereoscopic microscope.

9. Changes in Tumor Tissue after Injection with Oncolytic Adenovirus Expressing IL-12 and IL-23

Melanoma formed on the abdomen of male C57BL/6 mice as described in Example 6 "Examination of anti-tumor effects and survival rate ex vivo" was injected with adenovirus and then tumors were extracted about 5 days after last injection of virus. After tumors were lyophilized in O.C.T. compound and cut out 10 μm thickness, it was attached on gelatin-coated slides and histological immunostaining was performed. Tissues attached on slides were incubated with 0.3% hydrogen peroxide ($H_2O_2$) solution for 10 min to prevent endogenous peroxidase activity, and then with a rat anti-$CD4^+$ monoclonal antibody (Pharmingen) or a rat anti-$CD8^+$ monoclonal antibody (Pharmingen) as a primary antibody for 2 hrs at room temperature. It was incubated with a goat anti-rat IgG-HRP antibody (Pharmingen) as a secondary antibody for 1 hr at room temperature. Color was observed after addition of diaminobenzidene (DAB) and the slides were precipitated in 100%, 90%, 70% ethanol (EtOH) and xylene solution sequentially and then coverslipped.

Results

1. Preparation of Adenovirus Expressing IL-12 and IL-23 and Determination of IL-12 and IL-23 Expression Pattern To analyze whether anti-tumor effects of adenovirus expressing each IL-12 and IL-23 or IL-12 plus IL-23 were improved, each Ad-ΔB7/IL12 with inserted IL-12 into the E1 region of adenovirus, Ad-ΔB7/IL23 with inserted IL-23 into the E1 region of adenovirus, and Ad-ΔB7/IL23-p35 with inserted both IL-23 into the E1 region and p35 into the E3 region of adenovirus were constructed (FIG. 1). Ad-ΔB7/IL12, Ad-ΔB7/IL23, and Ad-ΔB7/IL23-p35 were oncolytic adenoviruses in which the E1B gene as an early gene of adenovirus is deleted and the E1A gene is mutated. Ad-ΔB7 is disclosed in the Korean Pat. Appln. No. 2004-0032638 filed by the present inventors and deposited in the Korean Culture Center of Microorganisms (KCCM) as Accession No. KCCM-10569.

Figure 2C:
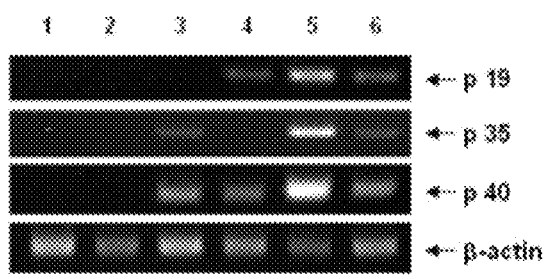
FIG. 2c represents RT-PCR analysis results of p19, p35 and p40 mRNA in U343 cells infected with Ad-ΔB7/IL23-p35 recombinant adenovirus. mRNAs from U343 cells infected with uninfected (lane 1), Ad-ΔB7 (lane 2), Ad-ΔB7/IL12 (lane 3), Ad-ΔB7/IL23 (lane 4), Ad-ΔB7/IL23-p35 (lane 5) and Ad-ΔB7/IL12 plus Ad-ΔB7/IL23 (lane 6) were analyzed.

To examine the expression level of IL-12 or IL-23 by the constructed adenovirus, human brain cancer cell U343 was infected with each adenoviruses (Ad-ΔB7/IL12, Ad-ΔB7/IL23, Ad-ΔB7/IL23-p35, and Ad-ΔB7/IL12 plus Ad-ΔB7/IL23) and after infection for 48 hrs, media were harvested and ELISA was performed. As described in FIGS. 2a and 2b, it was verified that IL-12 and IL-23 expression was consistent with infection of each virus. Especially, the expression level of IL-12 by infected with Ad-ΔB7/IL23-p35 (1 MOI: 3854±155 pg/mg) showed 14 times higher (than Ad-ΔB7/IL12) or 18 times higher (than Ad-ΔB7/IL12 plus Ad-ΔB7/IL23) than that infected with either Ad-ΔB7/IL12 (216±9 pg/mg) or Ad-ΔB7/IL12 plus Ad-ΔB7/IL23 (279±16 pg/mg) at 1 MOI. The expression level of IL-23 by infected with Ad-ΔB7/IL23-p35 (5 MOI: 17155±258 pg/mg) was increased each 46 times higher (than Ad-ΔB7/IL23) and 52 times higher (than Ad-ΔB7/IL12 plus Ad-ΔB7/IL23) than that infected with either Ad-ΔB7/IL23 (376±3 pg/mg) or Ad-ΔB7/IL12 plus Ad-ΔB7/IL23 (327±31 pg/mg) at 5 MOI.

To test the expression level of p19, p35, and p40 mRNA by the constructed adenovirus, human brain cancer cell U343 was infected with not only each Ad-ΔB7/IL12, Ad-ΔB7/IL23, and Ad-ΔB7/IL23-p35, but also Ad-ΔB7/IL12 plus Ad-ΔB7/IL23 (1:1 ratio mixture) at 5 MOI, respectively. After 48 hrs, cells were harvested and analyzed by RT-PCR analysis. As described in FIG. 2c, the expression of p19, p35, and p40 gene was confirmed as each infection of virus. Like the results of ELISA for IL-12 and IL-23 expression, it could be observed that as much as protein expression, the transcriptional expression of p19, p35, and p40 gene infected with Ad-ΔB7/IL23-p35 was exhibited higher than that infected with Ad-ΔB7/IL12, Ad-ΔB7/IL23, and Ad-ΔB7/IL12 plus Ad-ΔB7/IL23.

Figure 2D:
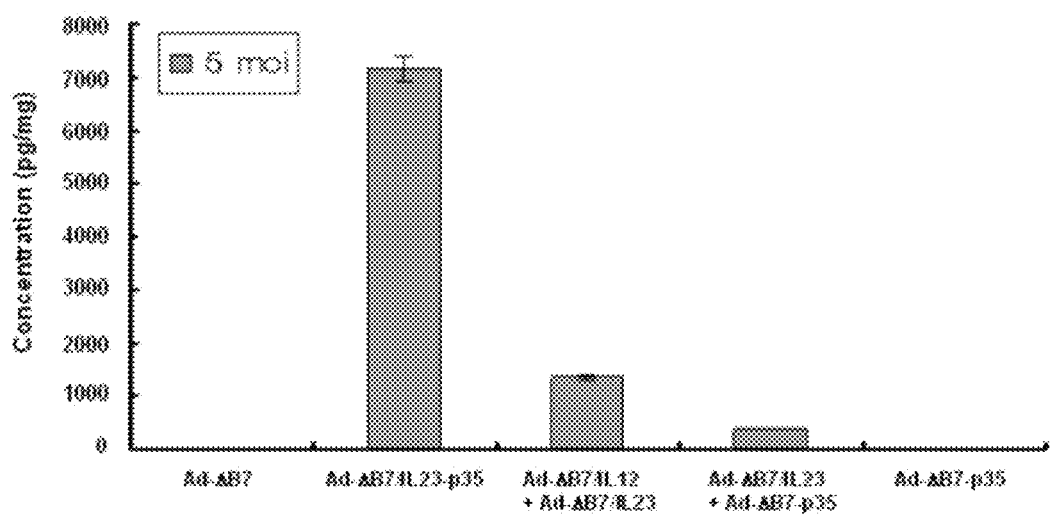
FIGS. 2d-2e demonstrate the gene-dose dependent increase in the expression levels of IL-12 and IL-23 by infection of Ad-ΔB7/IL23-p35 recombinant adenovirus.
Figure 2E:
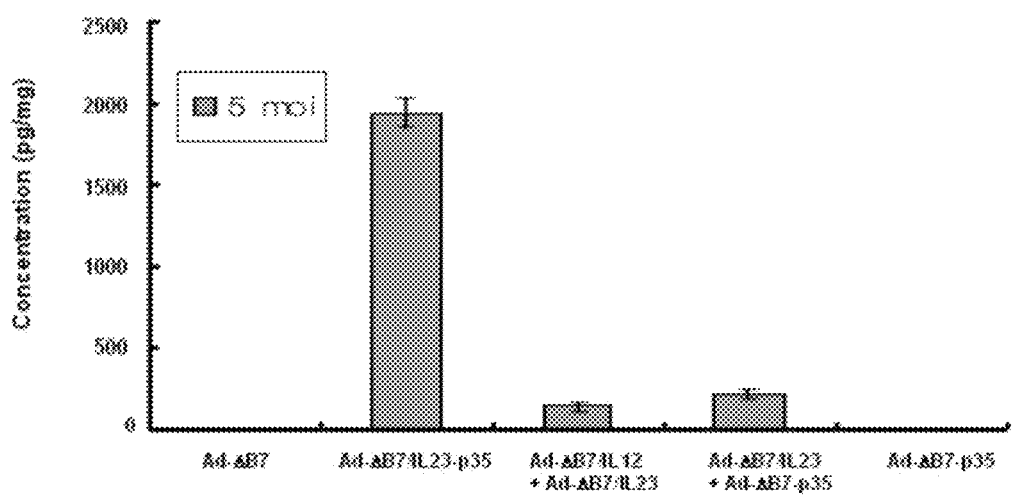

To determine whether the reason exhibiting higher expression of IL-12 and IL-23 infected with Ad-ΔB7/IL23-p35 than with Ad-ΔB7/IL12, Ad-ΔB7/IL23, and Ad-ΔB7/IL12 plus Ad-ΔB7/IL23 is relative to gene dose, human brain cancer cell U343 were infected with each adenoviruses (Ad-ΔB7, Ad-ΔB7/IL23-p35, Ad-ΔB7/IL12 plus Ad-ΔB7/IL23, Ad-ΔB7/IL23 plus Ad-ΔB7-p35, and Ad-ΔB7-p35) and after infection for 48 hrs, media were harvested and ELISA was performed. Ad-ΔB7-p35 is the adenovirus inserted p35 gene into the E3 region of Ad-ΔB7. As described in FIG. 2d-2e, it was observed that the amount of IL-12 expression when infected with Ad-ΔB7/IL23-p35 (5 MOI: 7170±250 pg/mg) was increased each 7 times higher (than Ad-ΔB7/IL23) and 20 times higher (than Ad-ΔB7/IL23 plus Ad-ΔB7-p35) than that with either Ad-ΔB7/IL12 plus Ad-ΔB7/IL23 (5 MOI: 1074±46 pg/mg) or Ad-ΔB7/IL23 plus Ad-ΔB7-p35 (5 MOI: 365±10 pg/mg). Likewise, it was observed that the level of IL-23 expression when infected with Ad-ΔB7/IL23-p35 (5 MOI: 1944±96 pg/mg) was increased each 9 times higher (than Ad-ΔB7/IL12 plus Ad-ΔB7/IL23) and 14 times higher (than Ad-ΔB7/IL23 plus Ad-ΔB7-p35) than that with either Ad-ΔB7/IL12 plus Ad-ΔB7/IL23 (5 MOI: 144±29 pg/mg) or Ad-ΔB7/IL23 plus Ad-ΔB7-p35 (5 MOI: 218±31 pg/mg). According to this result, it was shown that the coexpression of IL-23 and p35 with a single adenovirus vector could increase the expression levels of IL-12 and IL-23 compared with expression with separately different adenovirus vectors.

Figure 3A:
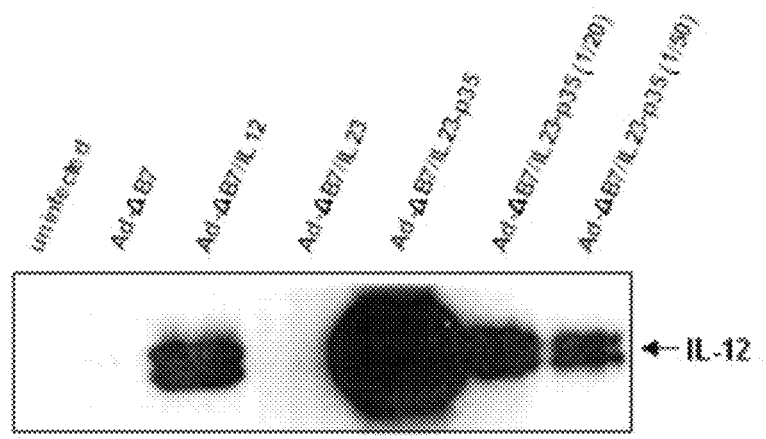
FIGS. 3a-3b show Western blotting results of the IL-12 and IL-23 protein expressed by Ad-ΔB7/IL23-p35 recombinant adenovirus vector. The number of parenthesis means dilution folds.
Figure 3A:
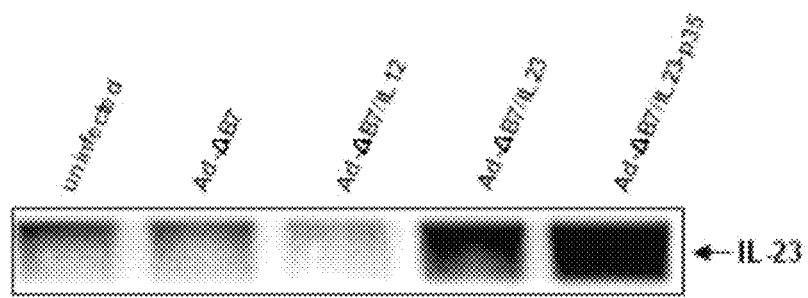
Figure 3B:
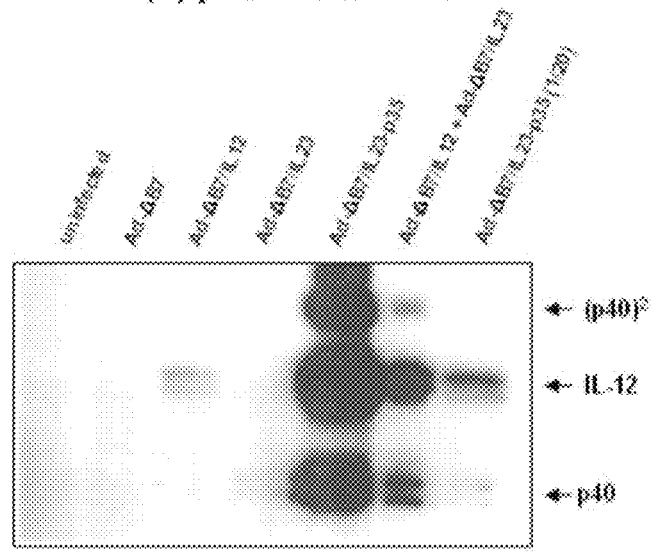
Figure 3B:
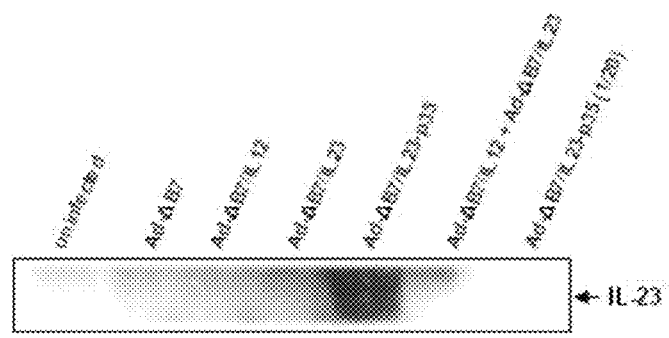

To examine the degree of IL-12 or IL-23 expression by the constructed adenoviruses, human brain cancer cell U343 was infected with each adenovirus (Ad-ΔB7/IL12, Ad-ΔB7/IL23, and Ad-ΔB7/IL23-p35) and after 48 hrs, media were harvested and Western blotting was performed. As described in FIG. 3a, the expression of 70 kDa IL-12 and 59 kDa IL-23 was observed each according to infection of each virus. Likewise the result of ELISA on IL-12 and IL-23, it was observed that the expression amount of IL-12 was increased remarkably in Ad-ΔB7/IL23-p35 than in Ad-ΔB7/IL12 and Ad-ΔB7/IL23. Especially, the expression amount of IL-12 infected with Ad-ΔB7/IL23-p35 was increased 20 times than that infected with Ad-ΔB7/IL12. Also, as described in FIG. 3b panel A and panel B, it was demonstrated that the expression amount of IL-12 and IL-23 infected with Ad-ΔB7/IL23-p35 at 5 MOI was increased considerably than that infected with Ad-ΔB7/IL12 plus Ad-ΔB7/IL23 at 5 MOI.

2. Analysis of in Vivo Anti-Tumor Effect of Adenovirus Expressing IL-12 and IL-23

To determine comparatively in vivo anti-tumor effect of each oncolytic adenoviruses, which was Ad-ΔB7/IL12 and Ad-ΔB7/IL23 expressing each IL-12 and IL-23, or Ad-ΔB7/

IL23-p35 expressing both IL-12 and IL-23, B16-F10 murine melanoma cell line was injected subcutaneous on the abdomen of male C57BL/6 mice, and the growth of tumors was observed by injecting each virus ($5 \times 10^9$ VP/30 μl) within formed tumors.

Figure 4A:
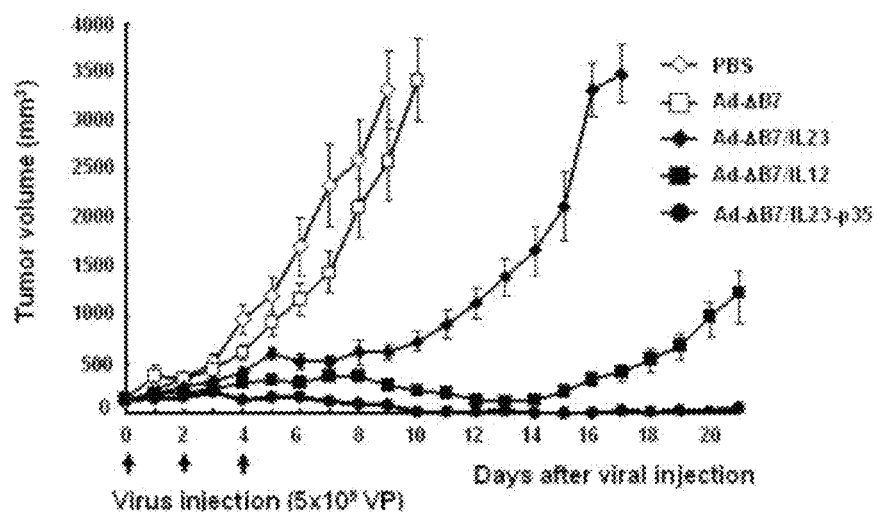
FIG. 4a represents in vivo anti-tumor effects of Ad-ΔB7/IL23-p35 recombinant adenoviruses in tumor-xenotransplanted mice.

In mice administered with PBS as a negative control, tumors grew at the rapid speed and the size of tumors was 3318±396.2 mm$^3$ at 9 days after injection of virus and no mouse was survived at 11 days. Additionally, in mice injected with oncolytic Ad-ΔB7 as a control, some inhibitory tendency was shown in the growth of tumors. However, tumors grew at the rapid speed as fast as PBS and the size of tumors was 2586.9±405.5 mm$^3$ at 9 days after injection of virus. In case of mouse injected with Ad-ΔB7/IL12 and Ad-ΔB7/IL23, the size of tumors was each 290.7±32.4 mm$^3$ and 623.3±83.3 mm$^3$ at 9 days after injection of virus, showing that tumors were inhibited remarkably in mice injected with Ad-ΔB7/IL12 than with Ad-ΔB7/IL23 (FIG. 4a). Especially, in mice injected with Ad-ΔB7/IL23-p35 inserted both IL-12 and IL-23, the size of tumors was each 79.2±19.6 mm$^3$ at 9 days after injection of virus, demonstrating that the growth of tumor was inhibited by injection of Ad-ΔB7/IL23-p35 more prominently than in that of each IL-12 and IL-23 and anti-tumor effects were improved more remarkably.

Figure 4B:
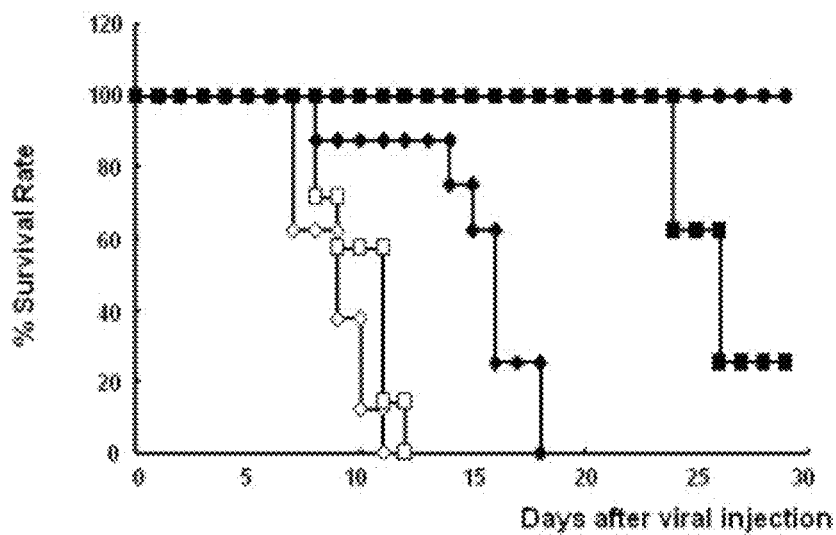
FIG. 4b represents survival rate after injection of Ad-ΔB7/IL23-p35 recombinant adenoviruses in tumor-xenotransplanted mice.

In represented in FIG. 4b to examine the survival rate of mouse, mice injected with PBS or Ad-ΔB7 were all died each at 11 or 12 days after injection, but mice with Ad-ΔB7/IL23 were all died at 18 days, demonstrating that the survival rate was increased in the Ad-ΔB7/IL23 than in PBS or Ad-ΔB7 as a control. The survival rate of mice injected with Ad-ΔB7/IL12 was 25% until 30 days after injection, showing that the survival rate was increased in Ad-ΔB7/IL12 than in the Ad-ΔB7/IL23. Especially, the survival rate of mice injected with Ad-ΔB7/IL23-p35 was 100% until 30 days after injection, demonstrating the survival rate of mice injected with Ad-ΔB7/IL23-p35 was improved significantly as anti-tumor effects.

3. Analysis of Tumor-Specific Immunity

Figure 5:
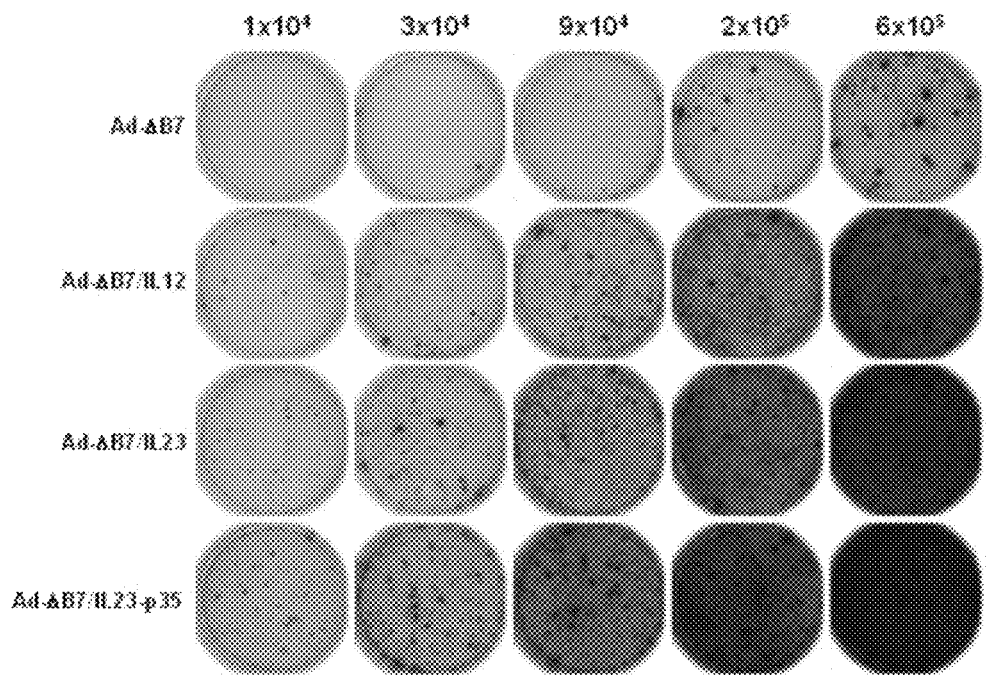
FIG. 5 indicates the result analyzing the occurrence frequency of tumor-specific IFN-γ-secreting immune cells by infection of Ad-ΔB7/IL23-p35 recombinant adenoviruses.
Figure 5:
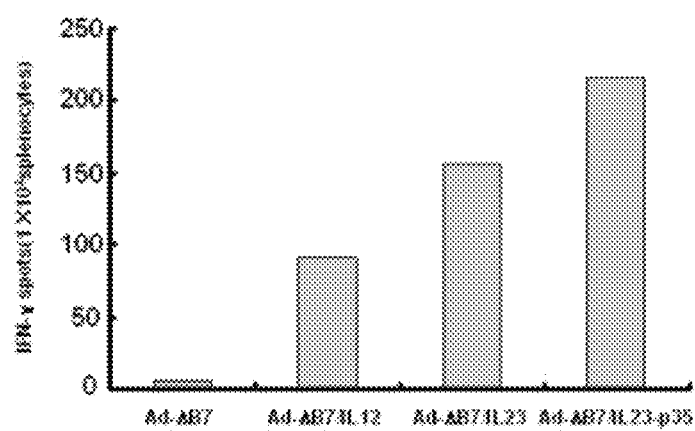

To determine the occurrence frequency of tumor-specific immune cells secreting IFN-γ, a cytokine secreted mainly by activated immune cells, IFN-γ ELISpot (enzyme-linked immune spot) analysis was performed (FIG. 5). $1 \times 10^4$, $3 \times 10^4$, $9 \times 10^4$, $2 \times 10^5$, and $6 \times 10^5$ splenocytes extracted from murine spleen injected with each virus were divided in 96-well plates coated with anti-IFN-γ antibody and counted the number of cells secreting IFN-γ. As described in FIG. 5, the increase of spleen cells was in proportion to that of the brown spot corresponding to IFN-γ secreting cells. It was observed especially that the number of brown spot in mouse injected with Ad-ΔB7/IL23-p35 was increased greater than with Ad-ΔB7, Ad-ΔB7/IL12, or Ad-ΔB7/IL23. In particular, the quantitative analysis of all wells loaded with $1 \times 10^4$ spleen cells showed that the number of brown spots observed in mice injected with Ad-ΔB7/IL23-p35 (216) was greater than those with Ad-ΔB7/IL12 (91) and Ad-ΔB7/IL23 (156), demonstrating anti-tumor immunity of mice injected with Ad-ΔB7/IL23-p35 was increased compared with Ad-ΔB7/IL12 and Ad-ΔB7/IL23.

4. Changes of Tumor Tissues after Injection of Replication-Competent Adenovirus Expressing IL-12 and IL-23

Figure 6:
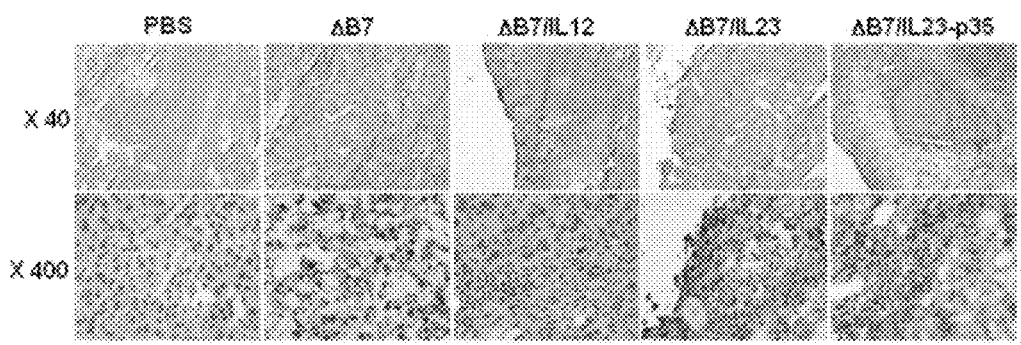
FIG. 6 represents the histologic analysis results stained with H & E staining after injection of Ad-ΔB7/IL23-p35 recombinant adenoviruses (oncolytic adenovirus expressing IL-12 and IL-23) in tumor-xenotransplanted mice.
Figure 7:
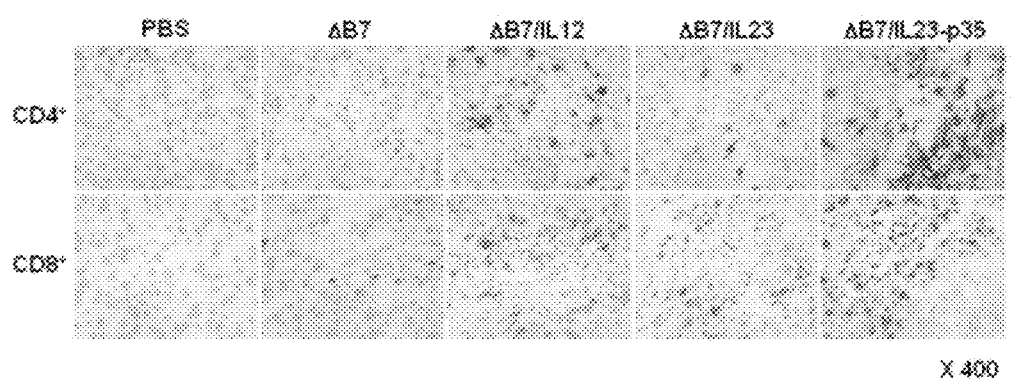
FIG. 7 represents immunohistological (IHE) analysis results stained with anti-CD4 and anti-CD8 antibodies after injection of Ad-ΔB7/IL23-p35 recombinant adenovirus (oncolytic adenovirus expressing IL-12 and IL-23) in tumor-transplanted mice.

To examine the changes within tumor tissue when IL-12 and IL-23 were expressed, lymphocytes infiltrated into tumors were investigated. As a result of H & E staining about tumor tissue injected with each viruses or PBS, it was observed that lymphocytes were not infiltrated into tumor tissues in the sample injected with PBS, but infiltrated into tumor tissues around in the samples injected with Ad-ΔB7/IL12 or Ad-ΔB7/IL23. Additionally, it was confirmed that in the samples of tumor tissues injected with Ad-ΔB7/IL23-p35 as compared with Ad-ΔB7/IL12 or Ad-ΔB7/IL23, many lymphocytes were penetrated notably not only surrounding, but inside tumor tissues, and most tumor cells were died (FIG. 6). To examine the population of lymphocyte penetrated into tumor tissues in more details, immunohistochemical (IHC) staining using anti-CD4$^+$ and anti-CD8$^+$ T-lymphocyte-specific antibodies was performed. It was then confirmed that CD4$^+$ and CD8$^+$ T-lymphocytes were observed not only inside but also surrounding tumor tissues injected with Ad-ΔB7/IL23-p35 as compared with Ad-ΔB7/IL12 or Ad-ΔB7/IL23, and number of T-lymphocytes in the sample injected with Ad-ΔB7/IL23-p35 was increased remarkably as compared to other samples (FIG. 7).

According to explanation above in detail, this invention provides the method and the expression vector for coexpressing IL-12 (interleukin-12) and IL-23 (interleukin-23) as described above, and the pharmaceutical anti-tumor compositions comprising the vector. The present invention co-expresses nucleotide sequences encoded the subunit composing of IL-12 and IL-23 using suitable monocistronic or polycistronic expression constructs at excellent efficiency. The cells transformed with the expression vector for IL-12 and IL-23 in the present invention displays the highest expression level of IL-12 and IL-23 protein. The expression vector of IL-12 and IL-23 in the present invention, especially, Ad-ΔB7/IL23-p35, shows excellent oncolytic effects, and exhibits very good effects as gene therapeutics for cancer.

Having described a preferred embodiment of the present invention, it is to be understood that variants and modifications thereof falling within the spirit of the invention may become apparent to those skilled in this art, and the scope of this invention is to be determined by appended claims and their equivalents.

References

1. Paillard F. Cancer gene therapy annual conference 1997: trends and news. *Human Gene Ther,* 9:283-286 (1998).
2. Grill J, Geoerger B, Lamfers M, Dirven C, Van Beusechem V, Gerritsen W, et al. Conditionally replicative adenoviruses: a second wind for cancer gene therapy. *Bull Cancer,* 90:1039-1048 (2003).
3. Verma I M, Somia N. Gene therapy-promises, problems and prospects. *Nature,* 389:239-240 (1997).
4. Ehrlich P. Ueber den jetzigen stand der karzinomforschung. Ned Tijdschr Geneeskd 5 (1909).
5. Gross L. Intradermal immunisation of C3H mice against a sarcoma that originated in an animal of the same line. *Cancer Res,* 3:326 (1943).
6. Burnet F M. Cancer-a biological approach. *BMJ,* 1:841 (1957).
7. Burnet F M. The concept of immunological surveillance. *Prog Exp Tumor Res* 13:1 (1970).
8. Thomas L. Cellular and humoral aspects of the hypersensitive states. New York: Hoeber-Harper; 1959.
9. Fearon E R, Pardoll D M, Itaya T, Golumbek P, Levitsky H I, Simons J W, et al. Interleukin-2 production by tumor cells bypasses T helper function in the generation of an anti-tumor response. *Cell,* 60:397-403 (1990).
10. Gansbacher B, Zier K, Daniels B, Cronin K, Bannerji R, Gilboa E. Interleukin 2 gene transfer into tumor cells abrogates tumorigenicity and induces protective immunity. *J Exp Med,* 172:1217-1224 (1990).
11. Tepper R I, Pattengale P K, Leder P. Murine interleukin-4 displays potent anti-tumor activity in vivo. *Cell,* 57:503-512 (1989).

12. Golumbek P T, Lazenby A J, Levitsky H I, Jaffee L M, Karasuyama H, Baker M, et al. Treatment of established renal cancer by tumor cell engineered to secrete interleukin-4. *Science*, 254:713-716 (1991).
13. Schmidt-Wolf I G, Huhn D, Neubauer A, Wittig B. Interleukin-7 gene transfer in patients with metastatic colon carcinoma, renal cell carcinoma, melanoma, or with lymphoma. *Hum Gene Ther*, 5:1161-1168 (1994).
14. Tahara H, Zitvogel L, Storkus W J, Zeh H J 3rd, Mckinney T G, Schreiber R D, et al. Effective eradication of established murine tumors with IL-12 gene therapy using a polycistronic retroviral vector. *J Immunol*, 154:6466-6474 (1995).
15. Colombo M P, Ferrari G, Stoppacciano A, Parenza M, Rodolfo M, Mayilio F, et al. Granulocyte colony-stimulating factor gene transfer suppresses tumorigenicity of a murine adenocarcinoma in vivo. *J Exp Med*, 173:889-897 (1991).
16. Dranoff G, Jaffee E, Lazenby A, Golumbek P, Levitsky H, Brose K, et al. Vaccination with irradiated tumor cells engineered to secrete murine granulocyte-macrophage colony-stimulating factor stimulates potent, specific, and long-lasting anti-tumor immunity. *Proc Natl Acad Sci USA*, 90:3539-3543 (1993).
17. Restifo N P, Spiess P J, Karp S E, Mule J J, Rosenberg S A. A nonimmunogenic sarcoma transduced with the cDNA for interferon gamma elicits CD8+ T cells against the wild-type tumor: correlation with antigen presentation capability. *J Exp Med*, 175:1423-1431 (1992).
18. Lee E, Trepicchio W L, Oestreicher J L, Pittman D, Wang F, Chamian F, et al. Increased expression of interleukin 23 p19 and p40 in lesional skin of patients with psoriasis vulgaris. *J Exp Med*, 199:125-130 (2004).
19. Pirhonen J, Matikainen S, Julkunen I. Regulation of virus-induced IL-12 and IL-23 expression in human macrophages. *J Immunol*, 169:5673-5678 (2002).
20. Oppmann B, Lesley R, Blom B, Timans J C, Xu Y, Hunte B, et al. Novel p19 protein engages IL-12p40 to form a cytokine, IL-23, with biological activities similar as well as distinct from IL-12. *Immunity*, 13:715-725 (2000).
21. Belladonna M L, Renauld J C, Bianchi R, Vacca C, Fallarino F, Orabona C, et al. IL-23 and IL-12 have overlapping, but distinct, effects on murine dendritic cells. *J Immunol*, 168:5448-5454 (2002).
22. Mattner F, Fischer S, Guckes S, Jin S, Kaulen H, Schmitt E, et al. The interleukin-12 subunit p40 specifically inhibits effects of the interleukin-12 heterodimer. *Eur J Immunol*, 23:2202-2208 (1993).
23. Gillessen S, Carvajal D, Ling P, Podlaski F J, Stremlo D L, Familletti P C, et al. Mouse interleukin-12 (IL-12) p40 homodimer: a potent IL-12 antagonist. *Eur J Immunol*, 25:200-206 (1995).
24. Lee H, Kim J, Lee B, Chang J W, Ahn J, Park J O, et al. Oncolytic potential of E1B 55 kDa-deleted YKL-1 recombinant adenovirus: correlation with p53 functional status. *Int J Cancer*, 88:454-463 (2000).
25. Kim J, Cho J Y, Kim J H, Jung K C, Yun C O. Evaluation of E1B gene-attenuated replicating adenoviruses for cancer gene therapy. *Cancer Gene Ther*, 9:725-736 (2002).

What is claimed is:

1. A method for coexpressing IL-12 (interleukin-12) and IL-23 (interleukin-23), which comprises the steps of:
   (a) preparing a polycistronic expression construct comprising nucleotide sequences encoding the p35 subunit, the p40 subunit and the p19 subunit;
   (b) transforming the polycistronic expression constructs into an isolated host cell; and
   (c) culturing the transformed host cell to obtain IL-12 and IL-23.

2. The method according to claim 1, wherein the polycistronic expression construct in the step (a) comprises (i) a promoter operable in a eukaryotic cell—a nucleotide sequence encoding a first one of the three subunits—a sequence encoding internal ribosomal entry site ("IRES")—a nucleotide sequence encoding a second one of the three subunits—IRES—a nucleotide sequence encoding a third one of the three subunits—a polyadenylation sequence, linked in this order.

3. The method according to claim 1, wherein the polycistronic expression construct in the step (a) comprises
   (i) a promoter operable in a eukaryotic cell a nucleotide sequence encoding a first one of the three subunits—IRES—a nucleotide sequence encoding a second one of the three subunits—a polyadenylation sequence, lined in this order, and
   (ii) a promoter operable in a eukaryotic cell—a nucleotide sequence encoding a third one of the three subunits —a polyadenylation sequence, linked in this order.

4. The method according to claim 3, wherein the polycistronic expression construct in the step (a) comprises the sequence selected from the group consisting of the following (i)-(vi):
   (i) (i-1) a promoter operable in a eukaryotic cell—a p19 encoding nucleotide sequence—IRES—a p40 encoding nucleotide sequence—a polyadenylation sequence, linked in this order, and
      (i-2) a promoter operable in a eukaryotic cell—a p35 encoding nucleotide sequence—a polyadenylation sequence, linked in this order;
   (ii) (ii-1) a promoter operable in a eukaryotic cell—a p40 encoding nucleotide sequence—IRES—a p19 encoding nucleotide sequence—a polyadenylation sequence, linked in this order, and
      (ii-2) a promoter operable in a eukaryotic cell—a p35 encoding nucleotide sequence—a polyadenylation sequence, linked in this order;
   (iii) (iii-1) a promoter operable in a eukaryotic cell—a p35 encoding nucleotide sequence—IRES—a p40 encoding nucleotide sequence—a polyadenylation sequence, linked in this order, and
      (iii-2) a promoter operable in a eukaryotic cell—a p19 encoding nucleotide sequence—a polyadenylation sequence, linked in this order;
   (iv) (iv-1) a promoter operable in a eukaryotic cell—a p40 encoding nucleotide sequenced—IRES—a p35 encoding nucleotide sequence—a polyadenylation sequence, linked in this order, and
      (iv-2) a promoter operable in a eukaryotic cell—a p19 encoding nucleotide sequence—a polyadenylation sequence, linked in this order;
   (v) (v-1) a promoter operable in a eukaryotic cell—a p19 encoding nucleotide sequence—IRES—a p35 encoding nucleotide sequence—a polyadenylation sequence, linked in this order, and
      (v-2) a promoter operable in a eukaryotic cell—a p40 encoding nucleotide sequence—a polyadenylation sequence, linked in this order; and
   (vi) (vi-1) a promoter operable in a eukaryotic cell—a p35 encoding nucleotide sequence—IRES—a p19 encoding nucleotide sequence—a polyadenylation sequence, linked in this order, and
      (vi-2) a promoter operable in a eukaryotic cell—a p40 encoding nucleotide sequence—a polyadenylation sequence, linked in this order.

5. The method according to claim 4, wherein the polycistronic expression construct in the step (a) comprises the sequence selected from the group consisting of the following (i) and (ii):
   (i-1) a promoter operable in a eukaryotic cell—a p19 encoding nucleotide sequence—IRES—a p40 encoding nucleotide sequence—a polyadenylation sequence, linked in this order, and
      (i-2) a promoter operable in a eukaryotic cell—a p35 encoding nucleotide sequence—a polyadenylation sequence, linked in this order; and
   (ii) (ii-1) a promoter operable in a eukaryotic cell—a p40 encoding nucleotide sequence—IRES—a p19 encoding nucleotide sequence—a polyadenylation sequence, linked in this order, and
      (ii-2) a promoter operable in a eukaryotic cell—a p35 encoding nucleotide sequence—a polyadenylation sequence, linked in this order.

6. The method according to claim 5, wherein the polycistronic expression construct in the step (a) comprises
   (i) (i-1) a promoter operable in a eukaryotic cell—a p19 encoding nucleotide sequence—IRES—a p40 encoding nucleotide sequence—a polyadenylation sequence, linked in this order, and
      (i-2) a promoter operable in a eukaryotic cell—a p35 encoding nucleotide sequence—a polyadenylation sequence, linked in this order.

7. The method according to claim 1, wherein the polycistronic expression construct in step (a) is derived from recombinant adenoviruses, adeno-associated viruses (AAV), retroviruses, lentiviruses, herpesviruses or vaccinia viruses.

8. The method according to claim 7, wherein the vector polycistronic expression construct in step (a) is derived from the recombinant adenoviruses.

9. The method according to claim 8, wherein the recombinant adenovirus comprises the deletion of the E1B region and the E3 region.

10. The method according to claim 6, wherein
the polycistronic expression construct comprising the sequence of the promoter operable in a eukaryotic cell—p19 encoding nucleotide sequence—IRES—p40 encoding nucleotide sequence—polyadenylation sequence, and the sequence of the promoter operable in a eukaryotic cell—p35 encoding nucleotide sequence—polyadenylation sequence is inserted into the E1B-deleted region or the E3-deleted region.

11. The method according to claim 6, wherein
the polycistronic expression construct comprising the sequence of the promoter operable in a eukaryotic cell—p19 encoding nucleotide sequence—IRES—p40 encoding nucleotide sequence—polyadenylation sequence, and the sequence of
the promoter operable in a eukaryotic cell—p35 encoding nucleotide sequence—polyadenylation sequence is inserted into the E3-deleted region.

12. The method according to claim 6, wherein the polycistronic expression construct in step (a) has a genetic map selected from the group consisting of FIGS. 1$d$-1$g$.

13. The method according to claim 9, wherein
the polycistronic expression construct comprising the sequence of the promoter operable in a eukaryotic cell—p19 encoding nucleotide sequence—IRES—p40 encoding nucleotide sequence—polyadenylation sequence and the sequence of the promoter operable in a eukaryotic cell—p35 encoding nucleotide sequence—polyadenylation sequence is inserted into the E1B-deleted region or the E3-deleted region.

14. The method according to claim 9, wherein
the polycistronic expression construct comprising the sequence of the promoter operable in a eukaryotic cell—p19 encoding nucleotide sequence—IRES—p40 encoding nucleotide sequence—polyadenylation sequence, and the sequence of
the promoter operable in a eukaryotic cell—p35 encoding nucleotide sequence—polyadenylation sequence is inserted into the E3-deleted region.

15. The method according to claim 9, wherein the polycistronic expression construct in step (a) has a genetic map selected from the group consisting of FIGS. 1$d$-1$g$.

* * * * *

```
SEQUENCE LISTING

<160> NUMBER OF SEQ ID NOS: 2

<210> SEQ ID NO 1
<211> LENGTH: 871
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)
<223> OTHER INFORMATION: _n is a or g or c or t
<220> FEATURE:
<221> NAME/KEY: misc_feature
<222> LOCATION: (25)
<223> OTHER INFORMATION: _n is a or g or c or t
<220> FEATURE:
<221> NAME/KEY: misc_feature
<222> LOCATION: (67)
<223> OTHER INFORMATION: _n is a or g or c or t
<220> FEATURE:
<221> NAME/KEY: misc_feature
<222> LOCATION: (80)
<223> OTHER INFORMATION: _n is a or g or c or t
<220> FEATURE:
<221> NAME/KEY: misc_feature
<222> LOCATION: (97)
<223> OTHER INFORMATION: _n is a or g or c or t
<220> FEATURE:
<221> NAME/KEY: misc_feature
<222> LOCATION: (112)
<223> OTHER INFORMATION: _n is a or g or c or t
<220> FEATURE:
<221> NAME/KEY: misc_feature
<222> LOCATION: (123)
<223> OTHER INFORMATION: _n is a or g or c or t
<220> FEATURE:
<221> NAME/KEY: misc_feature
<222> LOCATION: (166)
```

```
<223> OTHER INFORMATION: n is a or g or c or t
<220> FEATURE:
<221> NAME/KEY: misc_feature
<222> LOCATION: (811)
<223> OTHER INFORMATION: n is a or g or c or t
<220> FEATURE:
<221> NAME/KEY: misc_feature
<222> LOCATION: (820)
<223> OTHER INFORMATION: n is a or g or c or t
<220> FEATURE:
<221> NAME/KEY: misc_feature
<222> LOCATION: (832)
<223> OTHER INFORMATION: n is a or g or c or t
<220> FEATURE:
<221> NAME/KEY: misc_feature
<222> LOCATION: (837)
<223> OTHER INFORMATION: n is a or g or c or t
<220> FEATURE:
<221> NAME/KEY: misc_feature
<222> LOCATION: (838)
<223> OTHER INFORMATION: n is a or g or c or t
<220> FEATURE:
<221> NAME/KEY: misc_feature
<222> LOCATION: (853)
<223> OTHER INFORMATION: n is a or g or c or t
<220> FEATURE:
<221> NAME/KEY: misc_feature
<222> LOCATION: (857)
<223> OTHER INFORMATION: n is a or g or c or t
<220> FEATURE:
<221> NAME/KEY: misc_feature
<222> LOCATION: (860)
<223> OTHER INFORMATION: n is a or g or c or t
<220> FEATURE:
<221> NAME/KEY: misc_feature
<222> LOCATION: (863)
<223> OTHER INFORMATION: n is a or g or c or t
<220> FEATURE:
<221> NAME/KEY: misc_feature
<222> LOCATION: (866)
<223> OTHER INFORMATION: n is a or g or c or t
<220> FEATURE:
<221> NAME/KEY: misc_feature
<222> LOCATION: (870)
<223> OTHER INFORMATION: n is a or g or c or t

<400> SEQUENCE: 1 cccgccccccc taacgttact gnccnaagcc gcttggaata aggccggtgt gcgtttgtct      60
atatgtnatt ttcccccan attgccgttc ttttggncaa tgtaagggcc cnggaaacct     120
ggnccctgtc ttcttgacga gcattcctag ctagggtctt ttcccntctc gccaaaggaa     180
tgcaaggtct gtgaaatgtc gtgaaggaag cagttcctct ggaagcttct tgaagacaaa     240
caacgtctgt agcgacccttt gcaggcagc ggaaccccccc acctggcgac aggtgcctct     300
gcggccaaaa gccacgtgta taagatacac ctgcaaaggc ggcacaaccc cagtgccacg     360
ttgtgagttg gatagttgtg gaaagagtca aatggctctc ctcaagcgta ttcaacaagg     420
ggctgaagga tgcccagaag gtaccccatt gtatgggatc tgatctgggg cctcggtgca     480
catgctttac atgtgtttag tcgaggttaa aaaaacgtct aggccccccg aaccacgggg     540
acgtggtttt cctttgaaaa acacgatgat aatatggcca caaccatgag cttggcgaga     600
ttttcaggag ctaaggaagc taaaatggag aaaaaaatca ctggatatac caccgttgat     660
atatcccaat ggcatcgtaa agaacatttt gaggcatttc agtcagttgc tcaatgtacc     720
tataaccaga ccgttcagct ggatattacg gccttttttaa agaccgtaaa gaaaaataag     780
cacaagtttt atccggcctt tattcacatt ncttgcccgn cctgatgaat gntgcanncc     840
ggaattacat cgnatgnatn gggtnctgn c                                    871

<210> SEQ ID NO 2
```

```
<211> LENGTH: 139
<212> TYPE: DNA
<213> ORGANISM: Simian virus 40

<400> SEQUENCE: 2
ttcgagcaac ttgtttattg cagcttataa tggttacaaa taaagcaata gcatcacaaa        60
tttcacaaat aaagcatttt tttcactgca ttctagttgt ggtttgtcca aactcatcaa       120
tgtatcttat catgtctgg                                                    139
```